United States Patent [19]

Ahl et al.

[11] Patent Number: 5,614,214
[45] Date of Patent: Mar. 25, 1997

[54] REDUCTION OF LIPOSOME-INDUCED ADVERSE PHYSIOLOGICAL REACTIONS

[75] Inventors: Patrick L. Ahl, Princeton; Suresh K. Bhatia, Plainsboro; Sharma R. Minchey, Monmouth Junction, all of N.J.; Andrew S. Janoff, Yardley, Pa.

[73] Assignee: The Liposome Company, Inc., Princeton, N.J.

[21] Appl. No.: 247,053

[22] Filed: May 20, 1994

Related U.S. Application Data

[63] Continuation-in-part of Ser. No. 207,651, Mar. 7, 1994, abandoned, which is a continuation-in-part of Ser. No. 65,928, May 21, 1993, abandoned.

[51] Int. Cl.$^6$ ..................................................... A61K 9/127
[52] U.S. Cl. ................................... 424/450; 428/402.2
[58] Field of Search ..................... 424/450; 428/402.2; 436/829

[56] References Cited

U.S. PATENT DOCUMENTS

| | | | |
|---|---|---|---|
| 3,577,446 | 5/1971 | Rakhit | 260/403 |
| 3,993,754 | 11/1976 | Rahman et al. | 424/177 |
| 4,145,410 | 3/1979 | Sears | 424/19 |
| 4,224,179 | 1/1980 | Schneider | 252/316 |
| 4,229,360 | 10/1980 | Schneider et al. | 260/403 |
| 4,235,871 | 11/1980 | Papahadjopoulos et al. | 424/19 |
| 4,522,803 | 6/1985 | Lenk et al. | 424/1.1 |

(List continued on next page.)

FOREIGN PATENT DOCUMENTS

| | | | |
|---|---|---|---|
| 0213523 | 3/1987 | European Pat. Off. | A61K 9/50 |
| 0312212 | 4/1989 | European Pat. Off. | G01N 33/531 |
| 61-088887 | 5/1986 | Japan | A61K 3/127 |
| 85/00968 | 3/1985 | WIPO | A61K 9/22 |
| 86/00238 | 1/1986 | WIPO | B01D 13/00 |
| 86/01102 | 2/1986 | WIPO | A61K 9/60 |
| 87/00043 | 1/1987 | WIPO | A61K 9/00 |
| 87/02219 | 4/1987 | WIPO | A01N 25/28 |
| 88/06443 | 9/1988 | WIPO | A61K 9/66 |
| 88/09165 | 5/1989 | WIPO | A61K 9/50 |
| 90/14105 | 11/1990 | WIPO | A61K 43/00 |
| 92/05773 | 4/1992 | WIPO | A61K 9/127 |

OTHER PUBLICATIONS

Bangham, et al., "Diffusion of Univalent Ions across the Lamellae of Swollen Phospholipids", J. Mol. Biol., 13:238–252 (1965).

Deamer and Uster, "Liposome Preparation: Methods and Materials," in: *Liposomes*. Marcel Dekker, Inc., New York (1983) 27–51.

Ivancev et al, "Effect of Intravenously Injected Iodinated Lipis Emulsions on the Liver", Acta Radiologica, 30, (1989), 291–298.

Ivancev, et al., "Experimental Investigation of a New Iodinated Lipid Emulsions for Computed Tomography of the Liver", Acta Radiologica 30 (1989), Fasc. 4, pp. 407–413.

Mayer, et al., "Solute distributions and trapping efficiencies observed in freeze-thawed multimaller vesicles", Biochim. Biophys. Acta, 1985, 817:193–196.

Papahadjopoulos, et al., "Phospholipid Model Membranes, I. Structural Characteristics of hydrated Liquid Crystals", Biochim. Biophys. Acta, 1968, 135:624–638.

Park, et al., "Some negatively charged phospholipid derivatives prolong the liposome circulation time in vivo" Biochimica et Biophysica Acta, 1992, 1108(2), 257–60.

*Primary Examiner*—Gollamudi S. Kishore
*Attorney, Agent, or Firm*—Kenneth B. Rubin

[57] ABSTRACT

Provided herein is a method of administering a liposome composition to an animal, the method involving adminstering to the animal a liposome composition containing an adverse physiological reaction-reducing effective amount of a liposome which has, in addition to a bioactive agent, a lipid bilayer containing a lipid and a surface agent-modified molecule. An adverse physiological reaction which may be experienced by the animal upon administration of a liposome composition is reduced by way of the presence of the surface agent-modified molecule in the liposome's lipid bilayer.

18 Claims, 16 Drawing Sheets

U.S. PATENT DOCUMENTS

| | | | |
|---|---|---|---|
| 4,588,578 | 5/1986 | Fountain et al. | 424/1.1 |
| 4,721,612 | 1/1988 | Janoff et al. | 424/1.1 |
| 4,861,580 | 8/1989 | Janoff et al. | 424/1.1 |
| 4,880,635 | 11/1989 | Janoff et al. | 424/450 |
| 4,975,282 | 12/1990 | Bally et al. | 424/450 |
| 5,008,050 | 4/1991 | Cullis et al. | 264/4.3 |
| 5,013,556 | 5/1991 | Woodle et al. | 424/450 |
| 5,030,453 | 7/1991 | Lenk et al. | 424/450 |
| 5,041,278 | 8/1991 | Janoff et al. | 424/1.1 |
| 5,077,056 | 12/1991 | Balley et al. | 424/450 |
| 5,313,804 | 5/1993 | Martin et al. | 424/450 |

REDUCTION OF LIPOSOME-INDUCED ADVERSE PHYSIOLOGICAL REACTIONS

This application is a continuation-in-part of U.S. Ser. No. 08/207,651, filed Mar. 7, 1994, now abandoned, which in turn is a continuation-in-part of U.S. Ser. No. 08/065,928, filed May 21, 1993, now abandoned.

This invention relates to a method for the reduction of liposome induced adverse physiological reactions when liposome compositions are administered to animals, including mammals such as humans. These liposome compositions can be used to encapsulate bioactive agents.

Liposomes are completely closed lipid bilayer membranes containing an entrapped aqueous volume. The bilayer is composed of lipid molecules which comprise monolayers having a hydrophobic region and a hydrophilic region. The structure of the bilayer is such that the hydrophobic (nonpolar) acyl chain region of the lipid monolayers orient toward the center of the bilayer while the hydrophilic (polar) lipid headgroups orient towards the aqueous phase.

In a liposome-drug delivery system, a bioactive agent such as a drug is entrapped in the liposome and then administered to the patient to be treated (Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al, U.S. Pat. No. 4,588,578; the contents of these disclosures are incoporated herein by reference). Bioactive agents can be entrapped within the lipid bilayers of liposomes or in its aqueous compartments. Encapsulation of bioactive agents, especially therapeutic or diagnostic agents, in liposome compositions is a well established method for delivering these agents to particular sites within the body.

It is believed that liposomes can be internalized by the phagocytic cells of the reticuloendothelial system (RES). Liposomes have been recognized as useful for carrying contrast media to reticuloendothelial tissues in the liver, kidneys, lungs and spleen. Liposome encapsulated iodinated organic compounds have been injected into the circulatory system of a patient to opacify certain organs for diagnostic examination (Schneider et al., "Injectable Opacifying Liposome Composition," International Application No., PCT/EP88/00447, International publication no. WO 88/09165, published May 10, 1989, the reference describing various means for encapsulating Iodinated;

It has been recognized that with increasing particle size, 2–3 um of lipid emulsions, a relatively greater proportion of particles are phagocytosed in the liver and spleen, as opposed to the bone marrow. However, adverse physiological reactions have been observed following the infusion of iodinated lipid emulsions. Other studies have shown that a sulphur colloid with a mean size of 0.3 microns can be used without ill effects (see Ivancev et al. "Effect of Intravenously Injected Iodinated Lipid Emulsions on the Liver", *Acta Radiologica* 30 (1989) p. 291–298.

Negatively charged phospholipid derivatives have been studied for effectiveness on circulation time of liposomes (see Park et al. "Some negatively charged phospholipid derivatives prolong the liposome circulation time in vivo" *Biochimica et Biophysica Acta*, 1992, 1108 (2) p. 257–60, the reference teaching that some negatively charged phospholipids enhance the circulation time of their liposomes, whilst other negatively charged phospholipids decrease circulation time (see Abstract).

Methods of enhancing the blood circulation time of intravenously administered liposomes include adding to the liposome an amphipatic lipid derivatized with a polyalkylether (Woodie et al., U.S. Pat. No. 5,013,556 "Liposomes with Enhanced Circulation Time", issued May 7, 1991, the contents of which are incorporated herein by reference).

SUMMARY OF THE INVENTION

This invention provides a method of administering a liposome composition to an animal which comprises administering to the animal a liposome composition comprising an adverse physiological reaction-reducing effective amount of a liposome comprising a bioactive agent and a lipid bilayer having a lipid and a surface agent-modified molecule which comprises a surface-modifying agent and an anchor. The liposome used in the method of this invention typically has a diameter of from about 200 nm to about 5000 nm, more preferably, from about 400 nm to about 5000 nm, and most preferably, presently, from about 400 nm to about 1000 nm. Liposomes having such diameters are preferably interdigitation-fusion liposomes (IFVs), but can also be large unilamellar liposomes (LUVs) or multilamellar liposomes (MLVs). The concentration of the surface agent modified molecule in the bilayer is typically at least about 2 mole %, more preferably at least about 5 mole %, and most preferably at least about 10 mole %. Preferably, the adverse physiological reaction-reducing effective amount of the liposome is about 50 mg of the liposome per kg of the animal's body weight.

The surface-modifying agent is preferably a dicarboxylic acid, e.g., succinic acid, glutaric acid, adipic acid, bimelic acid, suberic acid, tartaric acid, mucic acid, tetrafluorosuccinic acid or hexafluoroglutaric acid, a monocarboxylic acid, e.g., acetic acid, propionic acid, butyric acid, valeric acid, glycolic acid, lactic acid, trifluoroacetic acid, pentafluoropropionic acid or heptafluorobutyric acid, or a sulfolipid, e.g., bis(succinimidooxycarbonyloxy) ethyl sulfone, N-succinimidyl-S-acetylthioacetate or 2-iminothiolane (Traut's reagent). Preferably, the surface-modifying agent is glutaric acid. The anchor is preferably a phospholipid; preferably, the phospholipid has saturated acyl chains. Presently preferred saturated acyl chains are palmitate chains. Preferably, the phospholipid anchor is dipalmitoyl phosphatidylethanolamine (DPPE). The anchor can also be an amphiphilic protein. The surface-modifying agent is preferably linked to the hydrophobic domain of the anchor.

The surface-modified molecule can comprise a spacer group, which is typically any organic entity containing one or more organic functional groups which are capable of attaching to the glycerol backbone of a phospholipid anchor and to the phosphate group of the phospholipid anchor. Typically, the functional group is an hydroxyl, thiol, epoxide or amine group; preferably, the spacer group is ethylene glycol or polyethylene glycol.

The liposome used in the method of this invention comprises a bioactive agent, which is typically a contrast agent, antibacterial agent, antiviral agent, antifungal agent, antiparasitic agent, tumoricidal agent, anti-metabolite, carbohydrate, polypeptide, peptide, protein, toxin, enzyme, hormone, neurotransmitter, glycoprotein, lipoprotein, immunoglobulin, immunomodulator, vasodilator, dye, radiolabel, radio-opaque compound, fluorescent compound, receptor binding molecule, anti-inflammatory agent, mydriatic compound, local anesthetic, narcotic, vitamin, nucleic acid, polynucleotide, nucleoside, nucleotide, MRI, radio or water soluble iodinated contrast agent, and mixtures and pharmaceutically acceptable salts thereof or mixture thereof. Preferably, the bioactive agent is a water-soluble iodinated contrast agent selected from the group consisting of iohexol, iopamidol, ioxoglate, iotrolan, loversol, iothalamate, iodimide, iodipamide, iopromide, metrizamide, iopentol, iodixanol, diatrizoate, iotroxic acid and mixtures and pharmaceutically acceptable salts thereof. More preferably, the water-soluble iodinated contrast agent is iotralan. Preferably, the liposome composition is administered by intravenous or intra-arterial administration.

This invention also provides a method of administering a liposome composition to an animal which comprises administering to the animal an anti-inflammatory agent and a liposome composition comprising an adverse physiological reaction-reducing effective amount of a liposome comprising a bioactive agent and a lipid bilayer having a lipid and a surface agent-modified molecule, wherein the anti-inflammatory agent is administered to the animal prior to administration of the liposome composition. In one embodiment of the invention, the anti-inflammatory agent is asteroid; in an alternative embodiment of the invention, the anti-inflammatory agent is a nonsteroidal anti-inflammatory agent, preferably, indomethacin. Preferably, the agent is administered to the animal intravenously or intra-arterially at most about 30 minutes prior to administration of the liposome composition.

DETAILED DESCRIPTION OF THE INVENTION

Figure 1:
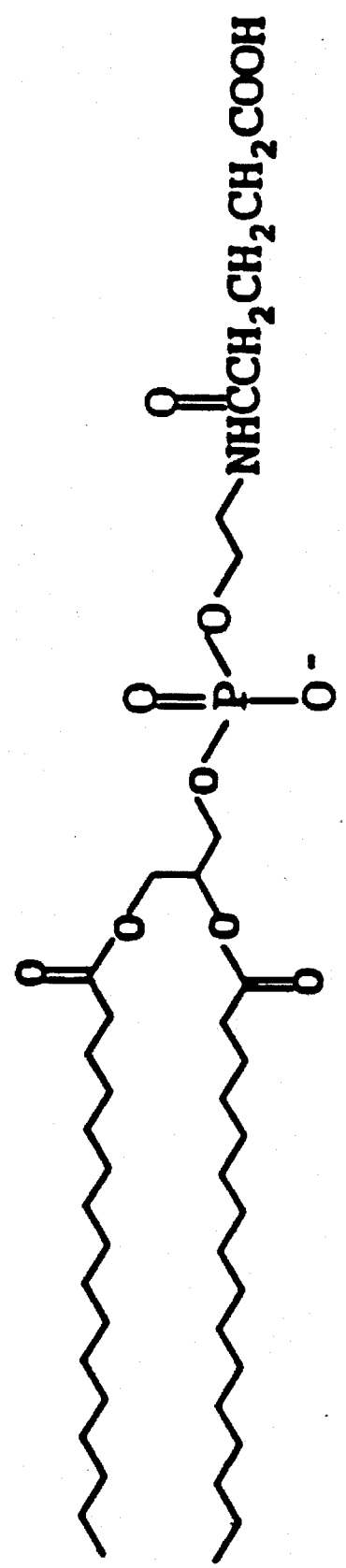
FIG. 1. Dipalmitoyl Phosphatidylethanolamine-Glutaric Acid (DPPE-GA).

This invention provides a method of administering a liposome composition to an animal which comprises administering to the animal a liposome composition comprising an adverse physiological reaction-inducing effective amount of a liposome comprising a bioactive agent and a lipid bilayer having a lipid and a surface agent-modified molecule. Adverse physiological reactions in animals have been associated with the administration of some liposome compositions to the animals. Such animals are preferably mammals, e.g., humans, but can also be any other animal to which liposomes can be administered. The term "adverse physiological reaction" includes, but is not limited to clinical symptoms such as lethargy, cyanotic gingival membranes, nausea, vomiting, defecation, diarrhea, rise in body temperature, fever, chills, shaking, somnolence, lower back pain, gastrointestinal disturbances, respiratory distress, hematological reactions such as neutropenia, thrombocytopenia, cardiovascular responses such as transient hypotension, vasodilation and transient cardiac changes.

The liposome used in the method of this invention preferably has a diameter of from about 200 nm to about 5000 nm, more preferably, from about 400 nm to about 1000 nm. It is known that larger liposomes tend, when administered to an animal, to be more rapidly cleared from the animal's circulation than are liposomes of similar composition, but smaller size. It is also known that certain modifications to a liposome's surface can enhance the time period over which the liposome remains in an animal's circulation. However, it has not heretofore been known that liposomes of sizes (diameters) as those used in the method of this invention are cleared from an animal's circulation at a rate comparable to that of unmodified (non-surface agent-modified molecule-containing) liposomes of similar size, and tend to accumulate to the same degree in the liver, but that in comparison to unmodified liposomes of similar size, administration of the liposomes of this invention can result in a reduction in adverse physiological reactions experienced by animals.

Liposomes used in the method of this invention are preferably interdigitation-fusion liposomes (IFVs), but can also be large unilamellar liposomes (LUVs) and multilamellar liposomes (MLVs); preferable MLVs are those which comprise a solute entrapped in their aqueous compartments, wherein the concentration of the solute in each of the aqueous compartments of the MLV is substantially equal, i.e., MLVs having substantially equal interlamellar solute distribution. The concentration of the surface agent-modified molecule in the bilayer is typically at least about 2 mole %, more preferably at least about 5 mole %, and most preferably at least about 10 mole %, mole % being calculated as the number of moles of surface agent-modified molecule in the bilayer divided by the total number of moles of compounds present in the bilayer.

It has been found that incorporating surface agent-modified molecules into liposomes in accordance with the practice of this invention results in significantly reduced adverse physiological reactions associated with the administration of some liposome compositions to animals. It has also been found that surface agent-modified molecules can be incorporated into liposomes without significantly affecting the high encapsulation capacity of larger liposomes, the shortened in vivo circulation times of larger liposomes, the imaging efficiency of liposomes containing radiological contrast agents and targeted to organs within an animal's body, the biodistribution of larger liposomes and their accumulation in an animal's liver, and without significantly interfering with the process of preparing interdigitation-fusion liposomes.

The liposome composition of this invention is a "surface-modified liposome composition," i.e., a liposome composition comprising a liposome containing a bioactive agent and a lipid bilayer comprising a lipid and a surface agent-modified molecule. The term "surface agent-modified molecule" is used herein to mean a molecule comprising a surface-modifying agent and an anchor. A "surface-modifying agent," as used herein, is any organic compound or entity capable of covalently linking at one end to the hydrophilic portion of the anchor. An "anchor," as used herein, is any molecule with a sufficient hydrophobic character to be stably inserted into a lipid bilayer and which also contains a hydrophilic portion suitable for modification with the surface-modifying agent, e.g., a hydrophilic portion containing a hydroxy, amine or thiol group. The surface-modifying agent is linked to a hydrophilic portion of the anchor and is also free to interact with the medium external to the liposome.

The surface agent-modified molecule is prepared by dissolving the anchor in solvent, for example chloroform, methylene chloride, acetonitrile, ethyl acetic, methanol, and the like, adding a base, for example triethylamine, dimethyl aminopyridine, pyridine, and the like, followed by adding the surface-modifying agent. The mixture is then allowed to react at room temperature while stirring, or by heating. The length of time for stirring or heating will vary with the particular surface-modifying agent used, and is determinable by one skilled in the art by means such as thin layer chromatography (TLC). Once the reaction is complete, as can be determined by TLC or any other method known in the art, the solvent is removed by heating on a rotary evaporator under vacuum. The product is removed by gel filtration or silica gel chromatography or ion exchange resin, or by any means known to one skilled in the art. The product is then lyophilized. This is one such method for the preparation of the surface modified molecule, other methods can be used by those skilled in the art given the teachings of this invention.

The surface-modifying agent is preferably a dicarboxylic acid, e.g., succinic acid, glutaric acid, adipic acid, bimelic acid, suberic acid, tartaric acid, mucic acid, tetrafluorosuccinic acid or hexafluoroglutaric acid, a monocarboxylic acid, e.g., acetic acid, propionic acid, butyric acid, valeric acid, glycolic acid, lactic acid, trifluoroacetic acid, pentafluoropropionic acid or heptafluorobutyric acid, or a sulfolipid, e.g., bis(succinimidooxycarbonyloxy) ethyl sulfone, N-succinimidyI-S-acetylthioacetate or 2-iminothiolane (Traut's reagent). Preferably, the surface-modifying agent is glutaric acid (see FIG. 1 ), which is preferably covalently linked to a hydrophilic portion of the anchor, e.g., by way of an amide linkage to the primary amine of a phosphatidylethanolamine group, e.g., dipalmitoyl phosphatidylethanolamine (DPPE). Accordingly, in a preferred embodiment of the invention, the surface-modified molecule comprises glutaric acid linked to DPPE (DPPE-GA). However, this invention is not limited to the use of DPPE-GA, but rather, can be practiced with any combination of surface-modifying agent and anchor.

The "anchor" can be any molecule with a hydrophobic portion of sufficient hydrophobic character to be stably inserted into a liposome's lipid bilayer, and a hydrophilic portion suitable for attaching to the surface-modifying agent. Preferably, the hydrophobic portion of the anchor comprises one or more fatty acid chains and the anchor is an amphiphilic lipid. Such lipids include, but are not limited to: phospholipids, glycolipids, sphingolipids including sphingomyelin, diacylammonium amphiphiles, diacyl glycerols, glycoshpingolipids, cerebrosides, sulfatides, ceramides, polyhexosides, gangliosides, sterols and the like. Preferably, the anchor is a phospholipid, i.e., an amphilic lipid with one or two acyl chains and a phosphate-containing glycerol backbone such as a phosphatidylcholine, phosphatidylethanolamine, phosphatidylglycerol, phosphatidylinositol or a phosphatidylserine; presently, the preferred phospholipid is a phosphatidylethanolaimne. Preferably, the phospholipid has saturated acyl chains, which are preferably palmitate chains. In a preferred embodiment of the invention, the phospholipid anchor is dipalmitoyl phosphatidylethanolamine (DPPE). The anchor can also be an amphiphilic protein or peptide. The surface-modifying agent is preferably linked to the hydrophilic domain of the anchor.

The surface-modified molecule can comprise a spacer group, which is typically any organic entity or moiety containing one or more organic functional groups which are capable of covalently attaching to the hydrophilic portion of the anchor, e.g., the glycerol backbone of a phospholipid anchor and to the phosphate group of the phospholipid anchor. Typically, the functional group is an hydroxyl, thiol, epoxide or amine group. Preferably, the functional group is a hydroxyl group, and the spacer group is ethylene glycol or polyethylene glycol, which can be of varying molecular weight.

Synthesis of spacer group-containing surface agent-modified molecules is accomplished by reacting the spacer group with a protecting agent, for example, methoxy-triphenylmethyl, acetyl or triphenylmethyl chloride (trityl chloride), etc, by means known to those with skill in the art. The phospholipid anchor is then activated by use of an activating agent, for example, p-nitrobenzene sulfonate, p-toluene sulfonate, benzene sulfonate, methane sulfonate, trifluoromethane sulfonate, and the like. The protected spacer group and the activated phospholipid anchor are then reacted by means known to those skilled in the art.

For example, the spacer group is introduced by using poly(oxyethylene), also called (poly)ethylene glycol. One of the two hydroxyl groups in (poly)ethylene glycol is protected by reacting ethylene glycol with 1 eq triphenylmethyl chloride (trityl chloride) in an organic solvent, preferably in the presence of a base such as triethylamine, to furnish monotritylated ethylene glycol. 1,2-Dipalmitoyl glycerol is then activated by a good leaving group, preferably using p-nitrobenzene sulfonyl chloride to give 1,2-dipalmitoyl-3-p-nitrobenzene sulfonate. This is then reacted with the monotritylated ethylene glycol followed by removal of the trityl group under mild acidic conditions. This results in the formation of 1,2-dipalmitoyl-3-(oxyethylene)glycerol. Two step procedure on this compound using 2-chloro-2-oxo-dioxphospholane and trimethylamine, respectively, introduces a choline moiety to generate the product.

The liposome used in the method of this invention comprises a bioactive agent, i.e., a compound or composition of matter having some biological activity in animals, including humans. The term bioactive agent includes traditional pharmaceuticals and related biologically active compositions of matter. Bioactive agents include, but are not limited to: antibacterial agents, antiviral agents, antifungal agents, antiparasitic agents, tumoricidal agents, anti-metabolites, carbohydrates, polypeptides, peptides, proteins, toxins, enzymes, hormones, neurotransmitters, glycoproteins, lipoproteins, immunoglobulins, immunomodulators, vasodilators, dyes, radiolabels, radio-opaque compounds, fluorescent compounds, polysaccharides, cell receptor binding molecules, anti-inflammatory agents, mydriatic compounds, local anesthetics, narcotics, anti-glaucomic agents, vitamins, nucleic acids, polynucleotides, nucleosides, nucleotides, MRI and radio contrast agents, water soluble iodinated contrast agents, including iohexol, iopamidol, ioxoglate, iotrolan, loversol, iothalamate, iodimide, iodipamide, iopromide, metrizamide, iopentol, iodixanol, diatrizoate, iotroxic acid, and mixtures, and pharmaceutically acceptable, salts thereof. Preferably, the bioactive agent is a water-soluble iodinated contrast agent selected from the group consisting of iohexol, iopamidol, ioxoglate, iotrolan, loversol, iothalamate, iodimide, iodipamide, iopromide, metrizamide, iopentol, iodixanol, diatrizoate and iotroxic acid. More preferably, the water-soluble iodinated contrast agent is iotralan. Preferably, the liposome composition is administered by intravenous or intra-arterial administration.

The lipid bilayer of the liposome used in the method of this invention comprises, in addition to the surface agent-modified molecule, a "lipid," which includes, but is not limited to: synthetic or natural phospholipids, glycolipids, glycerophospholipids, choline glycerophospholipids, ethanolamine glycerophospholipids, serine glycero phospholipids, inositol gylcerophospholipids, phosphatidylgylcerols, glycoglycerolipids, glycoglycerolipid sulfates, sphingolipids, sphingomyelin, diacyl ammonium amphiphiles, diacyl glycerols, glycosphingolipids, cerebrosides, sulfatides, ceramides, polyhexosides, gangliosides, phosphatidylcholine, phosphatidylethanolamine, phosphatidylserine, phosphatidylglycerol, phosphatidic acid, phosphatidylinositol, cardiolipin, and the like, alone, or in combination. The phospholipids can be synthetic, or derived from natural sources such as egg or soy. Useful synthetic phospholipids are dymyristoyl phosphatidylcholine and dimyristoyl phosphatidylglycerol. Distearyl phosphatidylcholine, dipalmitoyl phosphatidylcholine, dimyristoyl phosphatidylcholine, and diarachidonoyl phosphatidylcholine cany be used. The liposomes can also contain steroid components such as coprostanol, cholestanol, or cholestane, polyethylene glycol derivatives of cholesterol (PEG-cholesterols). They may also contain organic acid derivatives of sterols such as cholesterol hemisuccinate, and the like. Organic acid derivatives of tocopherols may also be used as liposome-forming ingredients, such as alpha-tocopherol hemisuccinate. Liposomes containing both organic acid derivatives of sterols, such as cholesterol hemisuccinate (CHS), and organic acid derivatives of tocopherols, such as tocopherol hemisuccinate (THS), as well as their tris salt forms, may generally be prepared by any method known in the art for preparing liposomes containing these sterols. In particular, see the procedures of Janoff, et al., U.S. Pat. No. 4,721,612 issued Jan. 26, 1988, entitled "Steroidal Liposomes," and Janoff, et al., U.S. Pat. No. 4,861,580, issued Aug. 29, 1989, and U.S. Pat. No. 5,041,278, issued Aug. 20, 1991, PCT Publication No. 87/02219, published Apr. 23, 1987, entitled "Alpha Tocopherol-Based Vehicles". The contents of these disclosures are incorporated herein by reference. A method for preparing sterol-containing liposomes involves adding to an aqueous buffer a salt form of an organic acid derivative of a sterol capable of forming closed bilayers in an amount sufficient to form completely closed bilayers which entrap an aqueous compartment. A suspension of multilamellar vesicles is formed by shaking the mixture. The formation of vesicles is facilitated if the aqueous buffer also contains the counterion of the salt in solution. Mayhew et al., PCT Publication No. WO85/00968, published Mar. 14, 1985, describes (see pp. 5–6) the preparation of liposomes containing alpha-tocopherol, at a molar ratio of alpha-tocopherol to total lipids of about 1:100, by mixing a phospholipid/chloroform solution with an alpha-tocopherol/chloroform solution, adding an aqueous solution to this mixture and then extruding the resulting liposomes under pressure through a 0.4-micron filter.

There are a variety of methods presently available for preparing liposomes and any may be useful in the practice of this invention. They include Bangham's method (see J. Mol. Biol. 13:238–252 (1965), of making multilamellar vesicles (MLVs). This method involves first forming a solution of lipids in an organic solvent and then evaporating the solvent, leaving dried lipid on the interior surface of the reaction vessel, to which an aqueous solution is added. Hydration of the lipid film results in the formation of MLVs.

Multilamellar vesicles may have substantially equal interlamellar solute distribution. The preparation of such MLVs is described in Lenk et al., U.S. Pat. Nos. 4,522,803 and 5,030,453, and Fountain et al., U.S. Pat. No. 4,588,708, the contents of these being incorporated by reference herein. Lenk et al. describe a process which involves mixing an aqueous solution of the substance to be entrapped with an organic solution of the lipid(s) being used to form the vesicles. The aqueous phase is then emulsified while the organic solvent is evaporated. Fountain's process involves first forming a solution of at least one amphipathic lipid and an aqueous component in an amount sufficient to form a monophase. The organic solvent is then evaporated, and a second aqueous component is added, with agitation, to form the liposomes.

This class of multilamellar liposomes can be denominated as stable plurilamellar liposomes (SPLV), as described in U.S. Pat. No. 4,522,803 to Lenk, et al., monophasic liposomes as described in U.S. Pat. No. 5,030,453 to Lenk et al. issued Jul. 9, 1991, and includes SPLV's in U.S. Pat. No. 4,558,579 to Fountain et al., and frozen-and-thawed multilamellar liposomes (FATMLVs), wherein the liposomes are exposed to at least one freeze and thaw cycle; this procedure is described in Cullis et al., U.S. Pat. No. 4,975,282, issued Dec. 4, 1990 and PCT Publication No. 87/00043, published Jan. 15, 1987, entitled "Multilamellar Liposomes Having Improved Trapping Efficiencies." The contents of these disclosures are incorporated herein by reference.

Preparation of small sonicated unilamellar vesicles has been described by Papahadjopoulos et al. (*Blochim. Biophys. Acta.*, 1968, 135:624–638), which teaches (see Abstract and p. 633) the production of smaller liposomes from larger liposomes by the application of sonication to a suspension of the larger liposomes. Large unilamellar vesicles may be produce apparatus by a method described in Cullis et al., U.S. Pat. No. 5,008,050, issued Apr. 16, 1991 and PCT Publication No. WO 86/00238, published Jan. 16, 1986, entitled "Extrusion Technique for Producing Unilamellar Vesicles," incorporated herein by reference. Vesicles made by this technique, called LUVETS, are extruded under pressure through a membrane filter. Vesicles may also be made by an extrusion technique through a 200 nm filter, such vesicles are known as $VET_{200}s$. These vesicles may be exposed to at least one freeze and thaw cycle prior to the extrusion technique; this procedure is described in Mayer, et al., (*Blochim. Biophys. Acta.*, 1985, 817:193–196), entitled "Solute Distributions and Trapping Efficiencies Observed in Freeze-Thawed Multilamellar Vesicles". The application of energy to the suspension, e.g. sonication, or extrusion of the vesicles through a French press cell or through a porous filter of the appropriate pore size, will convert the multilamellar sterol vesicles to unilamellar vesicles.

Unilamellar liposomes may be formed by a freeze-and-thaw technique followed by an extrusion through one or more polycarbonate filters. Liposomes of a predetermined size may also be formed by passing a suspension of liposomes under pressure through an one or more times through an aluminum oxide porous film, Coe et al. "Liposome Extrusion Process" U.S. patent application Ser. No. 771,267, a continuation-in-part of U.S. patent application Ser. No. 593,200 filed Oct. 5, 1990. Alternatively, LUVs can be formed by infusion, reverse-phase evaporation or detergent dilution techniques (Deamer and Uster, "Liposome Preparation: Methods and Materials," in: *Liposomes*, Marcel Dekker, Inc., New York (1983), pp. 27–51. Deamer and Uster teach LUV preparation by an infusion method involving infusion of a lipid/nonpolar solvent solution into an aqueous solution under conditions causing the solvent to vaporize, a reverse-phase evaporation method involving mixing organic and aqueous phases so as to form inverted lipid micelles and then evaporating the organic phase so as to form liposomes, and a detergent dilution method involving dispersing phospholipids in an aqueous medium with detergents and then removing the detergents by dialysis (see pp. 37–42). See, also Papahadjopoulos et al., U.S. Pat. No. 4,235,871, the contents of which are incorporated herein by reference.

Interdigitation-fusion liposomes (IFV's) and gels are useful in the practice of this invention and may be made according to the procedure disclosed by Boni et al., U.S. application Serial No. 07/961,277, filed Oct. 14, 1992. IFV's are formed by mixing a solute in the aqueous solvent with sized liposomes and adding an inducer to the aqueous solvent which causes the sized liposomes to fuse. The IF gel is than incubated above the phase transition temperature of the lipid thereby producing IFV's.

The liposome used in the method of this invention can be dehydrated. Liposomal dehydration can enable the vesicles to be stored for extended periods of time; dehydrated liposomes can then be reconstituted on an as-needed basis. Liposomes can be dehydrated, with freezing, using standard freeze-drying equipment, or its equivalents. Lyophilization is preferably carried out after incorporating one or more protective sugars into liposome preparations in accordance with the procedures described in Schneider et al. (U.S. Pat. No. 4,229,360) and Janoff et al., (U.S. Pat. No. 4,880,635), the contents of which are incorporated herein by reference). The protective sugar can be omitted if the dehydration is conducted without freezing and sufficient water is left remaining in the liposomal preparation to maintain the integrity of a substantial portion of the liposomal bilayers through the dehydration-rehydration process.

Hydrophilic bioactive agents can be entrapped in liposomes by dissolving the bioactive agent in the aqueous medium to which lipids are added. A portion of the bioactive agent will be encapsulated in the resulting liposomes as they are formed. Alternatively, the liposomes may first be prepared, and then loaded with ionizable bioactive agents by establishing a potential difference across the liposomal bilayer according to the methods of Bally et al., "Encapsulation of Antineoplastic Agents in Liposomes", U.S. Pat. No. 5,077,056, PCT application No. 85/01501, publication number WO 86/01102 published Feb. 27, 1986 the contents of which are incorporated herein by reference. Mayer et al. "High Drug:Lipid Formulations of Liposomal Encapsulated Antineoplastic Agent" PCT application number 88/00646, PCT publication number WO 88/06442, published Sep. 7, 1988 teaches (see Abstract) preparing liposomes in a first aqueous medium, acidifying the aqueous medium external to the liposomes so as to establish a pH gradient across their bilayers and then adding an ionizable antineoplastic agent to the liposome suspension. Madden et al., "Accumulation of Drugs into Liposomes by a Proton Gradient" PCT publication WO 90/14105 published Nov. 29, 1990, PCT application WO 90/02736, filed May 15, 1990; Madden describes (see pp. 9–13) loading ionizable drugs into liposomes by way of ion concentration gradients across the liposomes' bilayers, such loading proceeding to an extent that is greater than the solubility of the ionizable drug in the aqueous medium inside the liposomes. These techniques allow the loading of liposomes with ionizable bioactive agents to achieve interior concentrations considerably greater than otherwise expected from the drugs' solubility in aqueous solution at neutral pH and/or concentrations greater than can be obtained by passive entrapment techniques.

The method of this invention may be practiced with any of the above-described preparatory and loading techniques, or any other methods for making liposomes and loading them with drugs which are now known or later developed.

Figure 2:
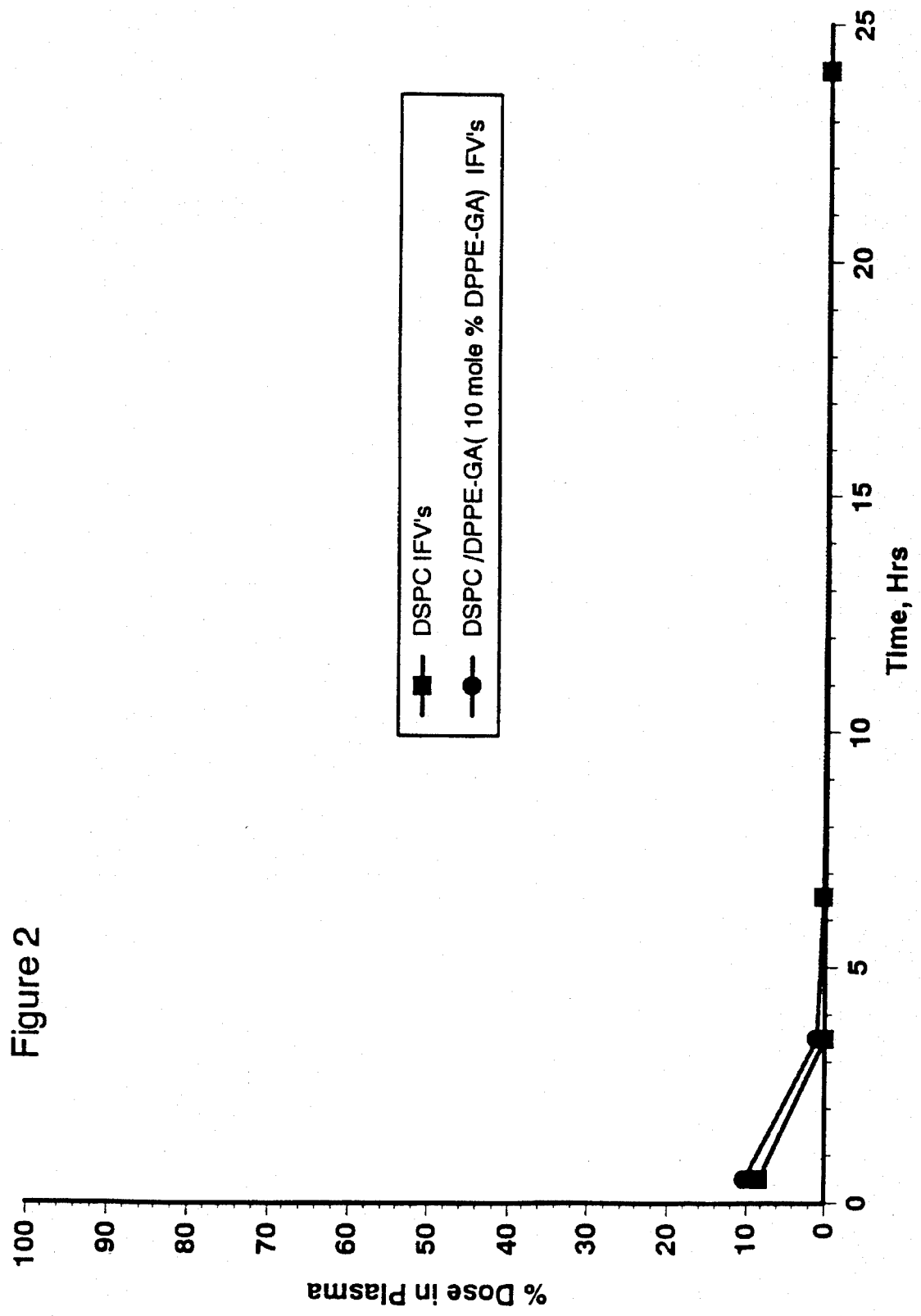
FIG. 2. Percentage Liposome Dose in Rat Plasma Following Injection of DSPC or DSPC/DPPE-GA Interdigitation-Fusion Liposomes (IFVs). Filled squares: DSPC IFVs; filled circles: DSPC/DPPE-GA (10 mole %)IFV's. X-axis: time (hours); y-axis: percent dose remaining in plasma.
Figure 3:
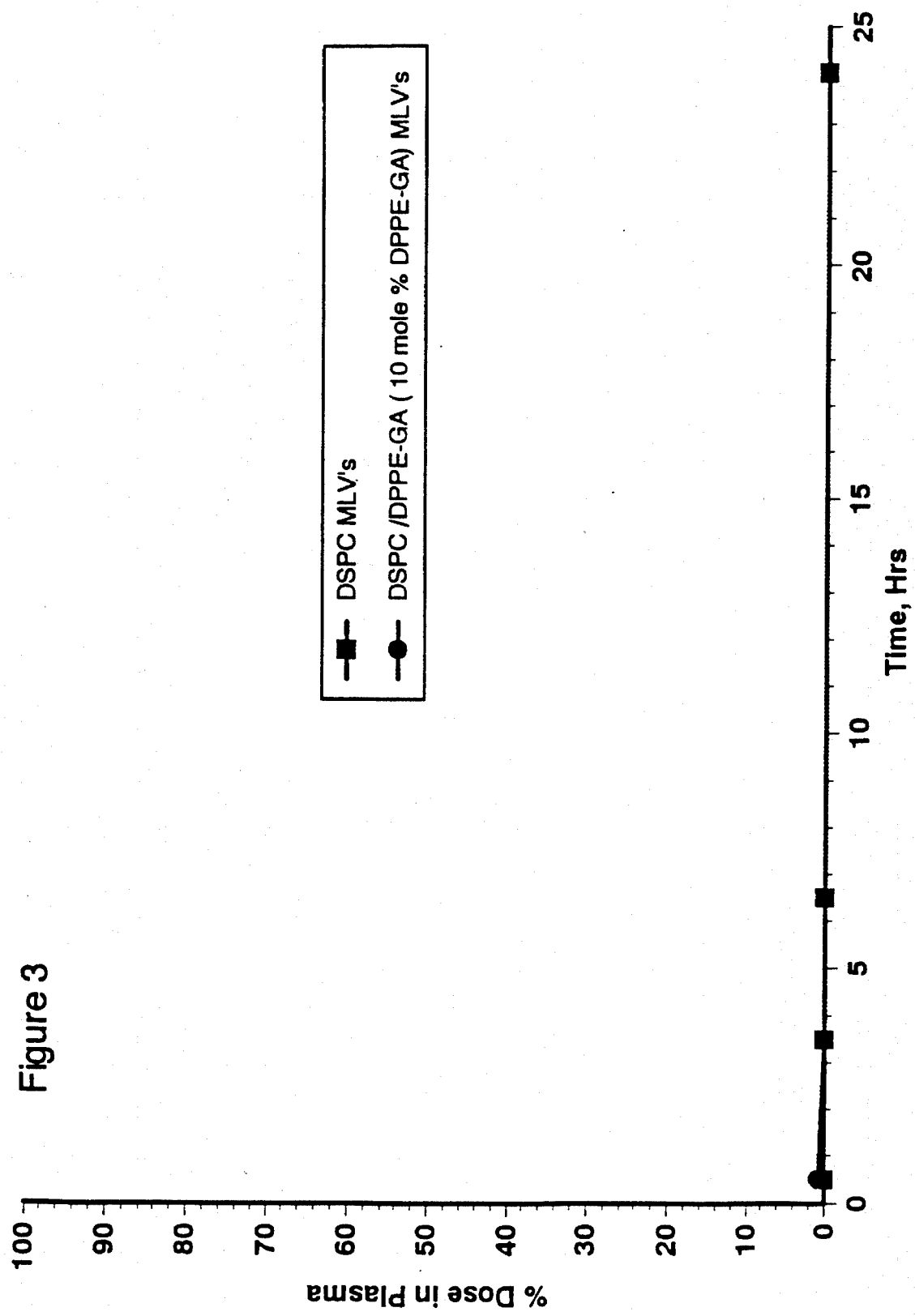
FIG. 3. Percentage Liposome Dose in Rat Plasma Following Injection of DSPC or DSPC/DPPE-GA Multilamellar Liposomes (MLVs). Filled squares: DSPC MLVs; filled circles: DSPC/DPPE-GA (10 mole %) MLV's. X-axis: time (hours); y-axis: percent dose remaining in plasma.
Figure 4:
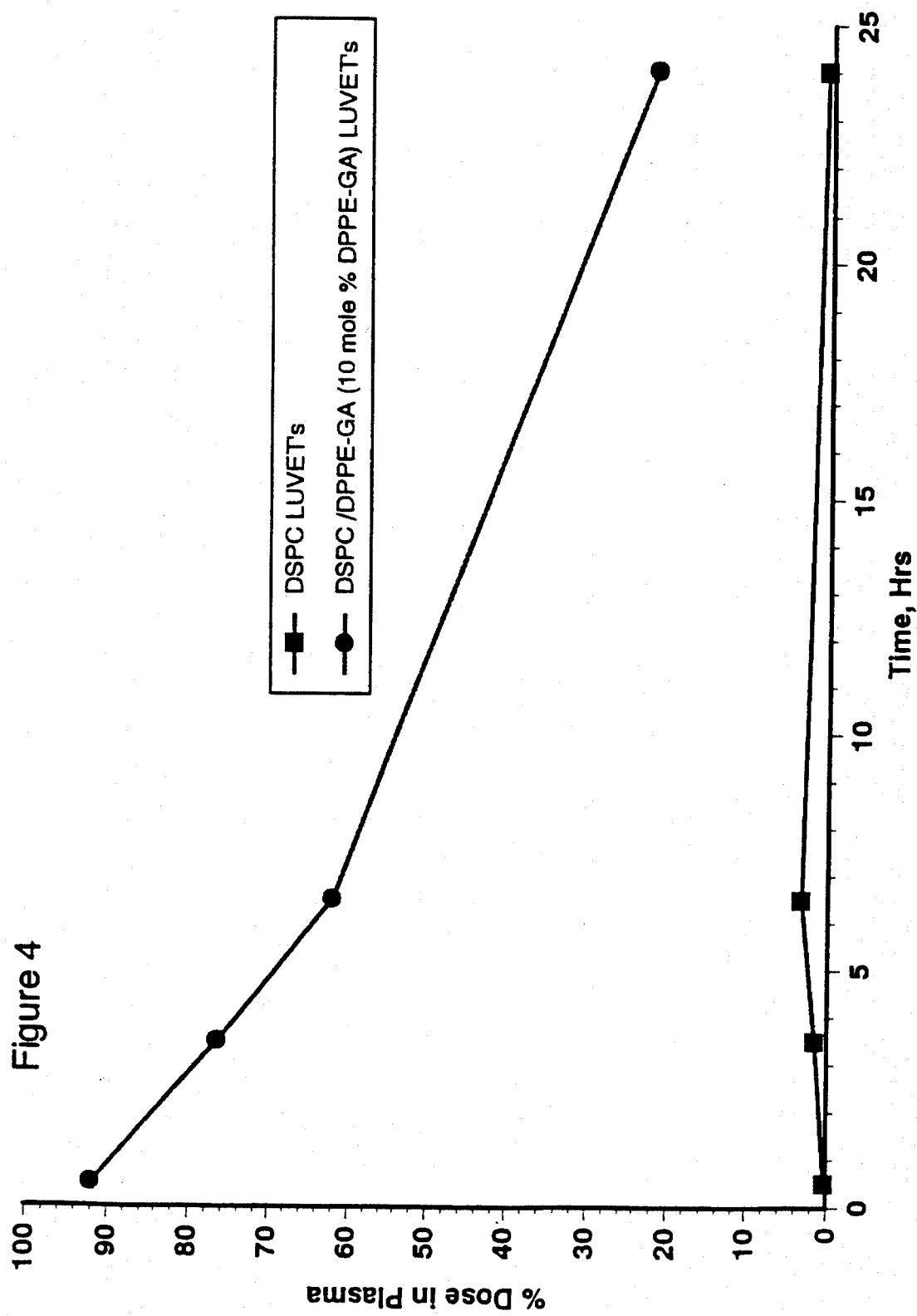
FIG. 4. Percentage Liposome Dose in Rat Plasma Following Injection of DSPC or DSPC/DPPE-GA Unilamellar Liposomes produced by Extrusion Technique (LUVETs). Filled squares: DSPC LUVETs; filled circles: DSPC/DPPE-GA (10 mole %) LUVET's. X-axis: time (hours); y-axis: percent dose remaining in plasma.

The incorporation of surface agent-modified molecules of the present invention into liposome compositions does not significantly alter the in vivo circulation time of certain liposomes. As shown in FIGS. 2 and 3, the average percentage of lipid dose remaining in rat plasma as a function of time after injection for both DSPC-IFV and DSPC-MLV's containing 10 mole percent of the surface agent-modified molecule DPPE-GA remained the same as for DSPC IFV's and DSPC MLV's without the surface agent modified molecule. However, as noted in FIG. 4, DSPC liposomes sized through a 0.2 micron filter containing 10 mole percent of the surface agent modified molecule DPPE-GA exhibited a prolonged circulation time as opposed to those vesicles not containing the surface agent modified molecule.

Figure 5:
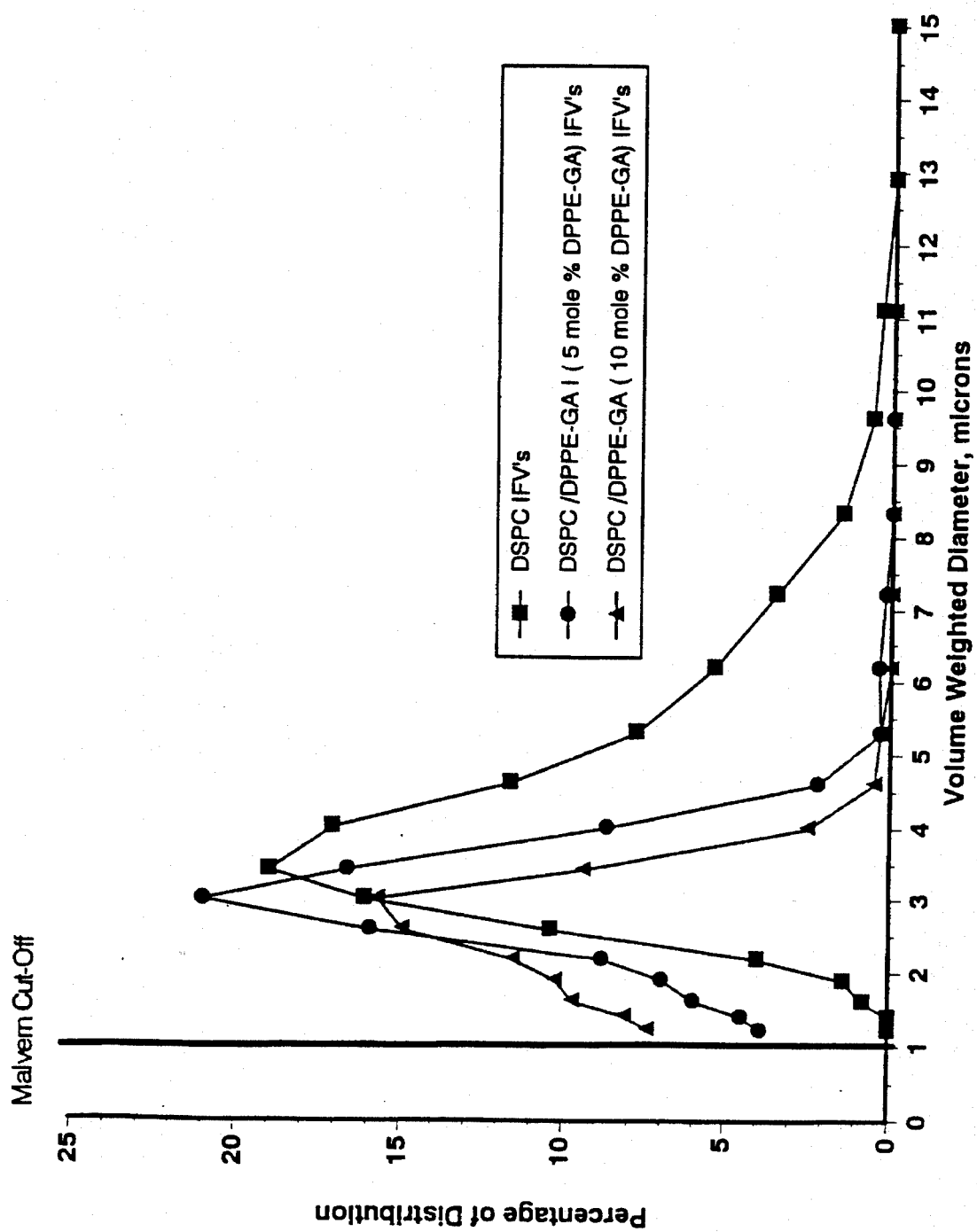
FIG. 5. Volume-Weighted Diameter of Iotrolan-Containing DSPC and DSPC/DPPE-GA IFV's. Filled squares: DSPC IFVs; filled circles: DSPC/DPPE-GA IFVs (5 mole % DPPE-GA); filled triangles: DSPC/DPPE-GA IFVs (10 mole % DPPE-GA). Thick vertical line represents Malvern cutoff. X-axis: Volume-weighted diameter (microns); y-axis: percentage of distribution.

Incorporation of surface agent-modified molecules does not interfere with the effectiveness of the process of preparing high captured volume liposomes, for example interdigitation-fusion liposomes. The radio contrast agent iotrolan was encapsulated in DSPC IFV's containing the surface agent-modified molecule DPPE-GA. The DSPC-IFV's, which contained 10 and 5 mole percent surface agent modified molecule DPPE-GA were prepared from DSPC/DPPE-GA SUV's in the presence of the radio contrast agent iotrolan. The presence of the surface agent-modified molecule did not interfere with the efficient encapsulation of iotrolan. As shown in Table 1, the iodine-to-lipid ratios obtained with DSPC/DPPE-GA IFV's were as high as the DSPC IFV's values lacking the surface agent-modified molecule. Incorporation of DPPE-GA did reduce the average volume-weighted diameter of the iotrolan DSPC IFV's, as shown in FIG. 5.

These iotrolan containing DSPC/DPPE-GA IFVs were effective in delivering the contrast agents to the liver and spleen of rats. Table 2 shows the Hounsfield Units (HU) enhancement values for rats dosed with Iotrolan containing DSPC/DPPE-GA IFV's at 5 and 10 mole percent of the surface agent modified molecule DPPE-GA. This data indicates that iotrolan DSPC IFV's modified to reduce adverse physiological reactions, such as transient hypotension, by the addition of a surface agent-modified molecule were effective in delivering contrast agents to target organs. Moreover, the incorporation of surface agent-modified molecules did not effect the imaging efficacy of the encapsulated radio contrast agent, as shown in Table 2.

The mode of administration of the liposome compositions of the present invention may determine the sites and cells in the organism to which the compound may be delivered. The liposome compositions of the present invention may be administered alone, or in admixture with a pharmaceutically acceptable carrier selected with regard to the intended route of administration and standard pharmaceutical practice. For parenteral administration or injection via intravenous, intraperitoneal, intramuscular, subcutaneous, or intra-mammary route, sterile solutions of the liposome composition are prepared. For intravenous use, the total concentration of solutes may be controlled to render the preparation isotonic. Other uses, depending upon the particular properties of the preparation, may be envisioned by those in the art. Suitable pharmaceutically acceptable carriers include, but are not limited to: water, salt solutions, alcohols, gum arabic, benzyl alcohols, gelatin, carbohydrates, such as lactose, amylose or starch, magnesium stearate, talc, silicic acid, hydroxy methylcellulose, polyvinyl pyrrolidone, and the like. The pharmaceutical compositions can be sterilized and if desired mixed with auxiliary agents, for example lubricants, preservatives, stabilizers, wetting agents, salts for influencing osmotic pressure, buffers, coloring, flavoring and/or aromatic substances and the like which do not deleteriously react with the bioactive agents or ingredients of this invention.

Administration of the liposome compositions of this invention may be by any method readily available in the art, including, but not limited to, parenterally, such as subcutaneously, intramuscularly, intraorbitally, intracapsularly, intraspinally, intrasternally, intravenously, intra-arterially, intrathecally and the like, orally, and topically.

The compositions of this invention are dispensed in unit dosage form comprising a therapeutically effective amount of bioactive agent in a pharmaceutically acceptable carrier per unit dosage. They are also incorporated in formulations comprising a therapeutically effective amount of bioactive agent. Therapeutically effective shall mean sufficient bioactive agent to achieve the desired biological result.

It will be appreciated that the actual preferred amounts of bioactive agents in a specific case will vary according to the specific compositions being utilized, the particular compositions formulated, the mode of application, and the particular situs and organism being treated. Dosages for a given host can be determined using conventional considerations, for example, by customary comparison of the differential activities of the subject compositions and of a known agent, for example by means of an appropriate, conventional pharmacological protocol. For administration to animals, including humans, the prescribing physician will ultimately determine the appropriate dosage of the bioactive agent for a given human subject, and this can be expected to vary according to the age, weight, and response of the individual as well as the pharmacokinetics of the agent used. Also the nature and severity of the patient's disease state or pharmacological condition will influence the dosage regimen. The amount, or dosage, of the surface agent-modified molecule-containing liposome used will be an "adverse physiological reaction-reducing effective amount", i.e., an amount effective to reduce an adverse physiological reaction experienced by an animal to which the liposome is administered. It can also depend upon the concentration of the surface agent-modified molecule in the lipid bilayer of the liposome. Typically, the adverse physiological reaction-reducing effective amount of the liposome as used in the method of this invention is about 50 mg of the liposome per kg of the animal's body weight, but can be higher, or lower, as necessary.

This invention also provides a method of administering a liposome composition to an animal which comprises administering to the animal an anti-inflammatory agent and a liposome composition comprising an adverse physiological reaction-inducing effective amount of a liposome comprising a bioactive agent and a lipid bilayer having a lipid and a surface agent-modified molecule, wherein the anti-inflammatory agent is administered to the animal prior to administration of the liposome composition. The anti-inflammatory agent can be administered by any method known in the art including by subcutaneous, intravenous daily or continuous intravenous infusion administration, but is preferably administered by intravenous administration. It may be administered with a pharmaceutically acceptable carrier or diluent. In one embodiment of the invention, the anti-inflammatory agent is asteroid; in an alternative embodiment of the invention, the anti-inflammatory agent is a nonsteroidal anti-inflammatory agent. Preferably, the nonsteroidal anti-inflammatory agent is indoemthacin. Preferably, the agent is administered to the animal intravenously or intra-arterially at most about 30 minutes prior to administration of the liposome composition.

This invention will be better understood from the following examples. However, those of ordinary skill in the art will readily understand that these Examples are merely illustrative of the invention as defined in the claims which follow thereafter.

EXAMPLES

Example 1

PREPARATION OF THE SURFACE MODIFYING AGENT DPPE-GLUTARIC ACID

A suspension of dipalmitoyl phosphoethanolamine (DPPE) (Avanti, Alabaster, Ala.) 692 mg (1 mmol) in anhydrous chloroform (125 ml) was heated at 50°–550° C. until it became a clear solution (15–20 min). After cooling this solution to room temperature, triethylamine (Fluka Chemicals, Ronkonkama, N.Y.) 190 µl (1.4 mmol) and glutaric anhydride (Fluka Chemicals, Ronkonkama, N.Y.) 137 mg (1.2 mmol) were added and the resulting solution and stirred at room temperature for 3 hours. Thin layer chromatography (TLC) of this reaction mixture was checked on silica plates to assess the progress of the reaction. After 3 hours, TLC revealed that all the DPPE had reacted.

At this point the chloroform was removed from the reaction mixture by heating on a rotary evaporator under vacuum. The residue was chromatographed on silica gel (activated by heating at 110° C. at least for 6 hours). The elution system was chloroform:methanol:water (65:25:4). The presence of phospholipid in column fractions was seen by exposing TLC plates first to iodine vapors, and then spraying with molybdic acid spray which gives blue color with phospholipids. Each fraction from the column was analyzed by TLC for the presence of phospholipid. The fractions containing the product were pooled and solvent removed under vacuum. The product was then freeze-dried and finally heated in vacuum oven at 60° C. for 6 hours to get a white crystalline material. Yield was 660 mg (82%).

Product DPPE-glutaric acid gave a single spot on TLC in solvent system chloroform:methanol:water (65:25:4) and was characterized by NMR and IR.

Example 2

PREPARATION OF DSPC/DPPE-GA IFV'S CONTAINING 0, 2, 5, AND 10 MOLE PERCENT DPPE-GA

Separate stock solutions of DSPC (20 mg/ml) and DPPE-GA (5 mg/ml) were prepared by dissolving the powdered forms of each lipid in chloroform. The DSPC was from purchased from Princeton Lipids, Princeton, N.J. DPPE-GA was prepared according to the procedures outlined in Example 1. Four DSPC/DPPE-GA samples were prepared by mixing the two chloroform stock solutions in four separate round bottom flasks. The total lipid content for each sample was 180 µM. The total amount for each lipid and the amount of stock solutions added for each sample are shown in the following Table.

| Label | DSPC µM | DPPE-GA µM | Stock DSPC ml | Stock DPPE-GA ml |
|---|---|---|---|---|
| BP1 (0% GA) | 300 | 0 | 11.85 | 0 |
| BPG2 (10% GA) | 162 | 18 | 6.399 | 2.898 |
| BPG3 (5% GA) | 171 | 9 | 6.755 | 1.45 |
| BPG4 (2% GA) | 176.4 | 3.6 | 6.968 | 0.58 |

The chloroform was removed on a rotary evaporator using a rotovac. The lipids were dried to a thin film. The samples were vacuum pumped overnight to remove any residual chloroform. The DSPC sample (BP1) was hydrated above the transition temperature (Tm) of DSPC with 10 ml of 0.9% saline for injection. The other three samples were hydrated above the Tm of DSPC with 6 ml or 0.9% saline for injection. This resulted in a total lipid concentration of 30 µM/ml for all four samples. At this point in the preparation the liposomes were MLV's. All four samples were treated in an identical manner for the rest of the preparation.

The samples were sonicated above the Tm of DSPC to form SUV's using a Branson probe sonicator model 450 (Branson, Danbury, Conn.). The liposome samples were sonicated until they were optically clear. A low speed (2K RPM) centrifugation was done using a table top centrifuge in order to remove metal flakes produced by the sonication step. The pH of each sample was adjusted with 0.1N NaOH and pH paper to bring the pH into the 6.5 to 7.0 range.

The temperature of the samples was allowed to reach room temperature. Sufficient ethanol was added to each sample to bring the ethanol concentration up to 3.0 M, i.e., 2.12 ml and 1.27 ml for the 10 ml and 6 ml sample case, respectively. The samples were sealed with a cap, and then vortexed to insure that the ethanol was uniformly mixed throughout the sample. The samples were incubated for 20 minutes at room temperature. After the 20 minute room temperature incubation the samples were transferred to a 70 C water bath where they were incubated for 10 minutes with a tight seal followed by a 40 minute 70 C incubation with the cap loosened.

The sample were give a 5 minute $N_2$ "sparge" by bubbling a gentle stream of $N_2$ through the sample while samples were still in the 70 C water bath. After the sparge step samples BP1 ( 0% DPPE-GA) and BPG4 (2% DPPE-GA) were transferred to 30 ml Corex glass centrifuge tubes. The samples were washed three times by centrifugation at 9K RPM for 10 minutes using a Beckman J-2 Centrifuge (Beckman, Palo Alto, Calif.). The 5% and 10% DPPE-GA liposomes (samples BPG2 and BPG3) would not pellet at 9K RPM using the low speed Beckman J-2 centrifuge. Therefore, these two samples were washed three times by ultracentrifugation at 25K RPM for 15 minutes using a Beckman L5-50E SW27 rotor (Beckman, Palo Alto, Calif.). The samples were resuspend in 0.9% saline for injection (10 ml for BP1 and 6.0 ml for all the rest). The pH was checked again to ensure that it was in the 6.5 to 7.0 pH range. A phosphate determination was made to determine the lipid concentration. Once the phosphate concentration for each sample was known the samples were ready for injection into animals.

Example 3

DSPC IFV INDUCED BLOOD PRESSURE RESPONSE IN RATS: EFFECT OF DPPE-GA INCORPORATION

Intravenous injection of DSPC IFV's at 50 mg/Kg induces a rapid blood pressure decrease in rats. Incorporation of the phospholipid dicarboxylic acid derivative DPPE-GA(3) into DSPC IFV's was found to significantly reduce this blood pressure decrease. In this example, we describe our experimental procedures and results for these rat blood pressure measurements.

Three days prior to the blood pressure experiment canulae were inserted into the aorta and jugular vein of spontaneous hypertensive rats. The rats were in the 350 to 400 gram range. The canulae were exteriorized at the back of the neck through a metal tether for protection. Heparinized saline was flushed through the canulae daily to prevent blockage.

Prior to the liposome injection the aortic canula was connected to a Winston Electronic pressure transducer (Winston Electronics, Millbrae, Calif.) to monitor mean aortic pressure (MAP). The jugular vein canula was connected to a 3 ml syringe which contained the IFV sample mounted in a Harvard Apparatus infusion pump (Harvard, South Natic, Mass.). The MAP of the rat was monitored a few minutes prior to the injection of the liposomes.

The infusion of the IFV's in to the jugular vein was started at time zero by turning on the infusion pump. The total lipid dose and dose rate for each animal was 50 mg/Kg and 4 mg/Kg/min, respectively. The lipid concentration of the samples was typically in the 10 to 15 mg/ml range. A typical injection was about 1 to 2 ml of IFV sample over a 12 minute period. The MAP was recorded every 30 seconds by the pressure transducer.

Figure 6:
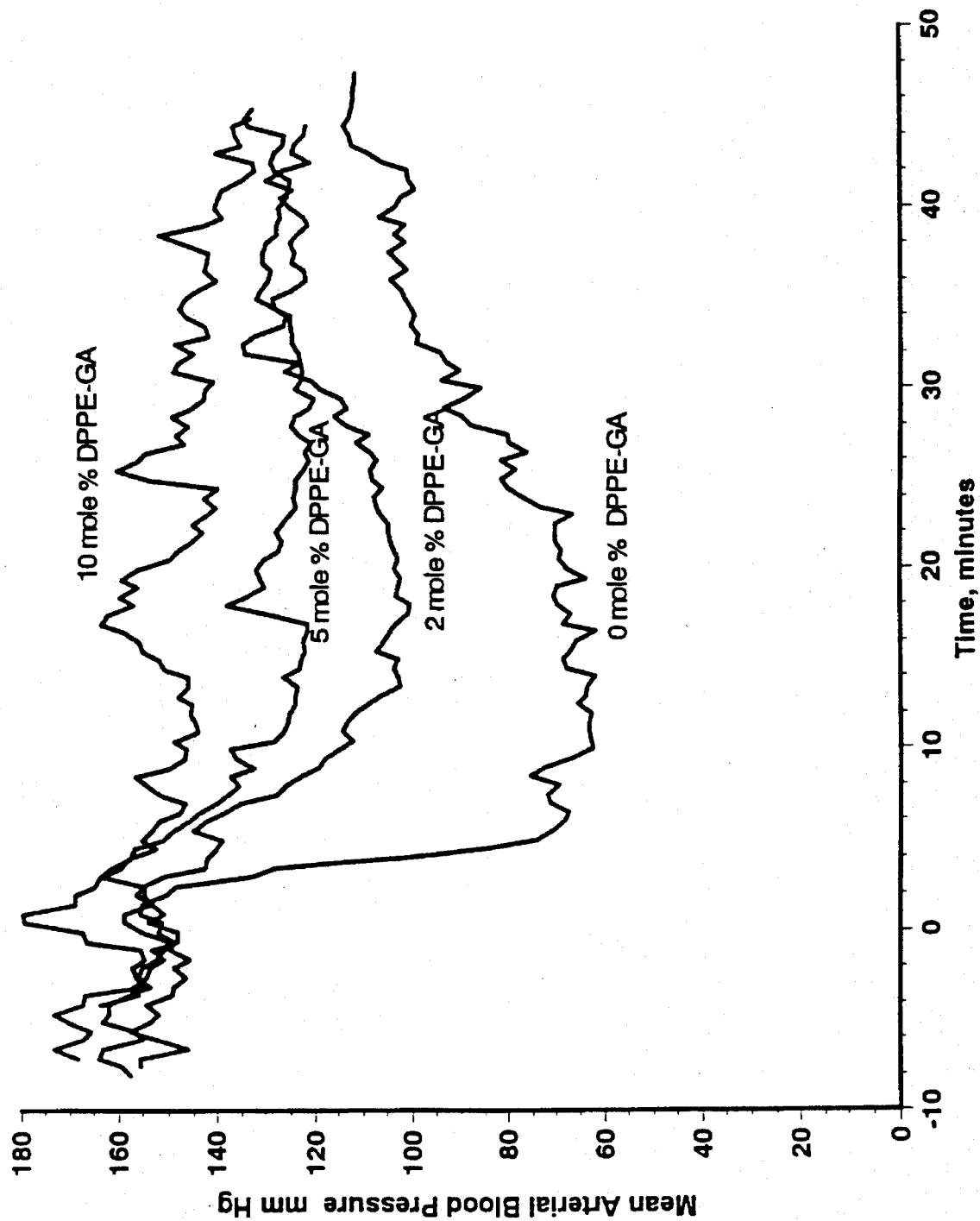
FIG. 6. Blood Pressure Changes Induced by DSPC and DSPC-GA IFVs. Traces (top to bottom): 10 mole % DPPE-GA; 5 mole % DPPE-GA; 2 mole % DPPE-GA; 0 mole % DPPE-GA. X-axis: Time (minutes); y-axis: mean arterial blood pressure (mm Hg).

As noted in Table 3, saline infusion (1.5 ml over 12 minutes) did not induce a drop in the MAP. In contrast, infusion of DSPC IFV's resulted a large decrease in the MAP which persisted over 50 to 60 minutes, FIG. 6. The average maximum MAP decrease for DSPC IFV's was 56±5.0%, Table 3. The DSPC IFV-induced MAP drop was significantly reduced when DPPE-GA was included in IFV formulation. Increasing the DPPE-GA content of the IFV's significantly increased the effect. This is shown in FIG. 6. The results are shown in Table 3.

FIG. 6 shows typical rat blood pressure responses to intravenous injections of DSPC IFV formulations which contained 10, 5, 2 and 0 mole percent DPPE-GA, as prepared in Example 2. Table 3 shows the mean arterial blood pressure decrease for the 10% DPPE-GA IFV's was 8.3±2.1%. The data in Table 2 clearly shows that a phospholipid dicarboxylic acid derivative reduced the blood pressure decrease induced by the DSPC IFV's.

Example 4

ADMINISTRATION OF INDOMETHACIN TO REDUCE BLOOD PRESSURE DROP WITH INTRAVENOUS INJECTION OF DSPC IFV'S

Intravenous injection of DSPC IFV's / 0% GA (50 mg/kg), prepared according to Example 2, into Wistar spontaneous hypertensive rats produces a rapid transient blood pressure drop.

The blood pressure drop in response to a DSPC IFV injection typically started at about 4 to 6 minutes after injection. A 30 to 40% drop of the initial blood pressure typically occurred over a 3 to 4 minute period. The blood pressure typically started to recover 20 to 25 minutes after the DSPC injection. The blood pressure recovery was not complete after 30 to 40 minutes.

An intravenous injection of the anti-inflammatory agent indomethacin (5 mg/kg) was given either 15 or 30 minutes prior to the injection of DSPC IFV's and produced a significantly different blood pressure response. After an initial small decrease the pressure quickly recovered back to the initial blood pressure within 30 to 40 minutes.

Example 5

NORMALIZED AUC'S OF DSPC/N-GLUTARYL-DPPE LIPOSOMES AS A FUNCTION OF AVERAGE LIPOSOME DIAMETER

LUVETS (LUVs prepared by extrusion technique) were prepared by extruding liposomes through polycarbonate filters with the following pore diameters 50, 80, 200, 400, 600, and 800 nm. The IFVs were prepared by the interdigitation-fusion technique. The average diameters of the LUVETs and IFVs were determined by quasi-elastic light scattering and freeze-fracture electron microscopy. The liposomes were radiolabeled with $^3$H-cholesterol hexadecyl ether, which is non-exchangeable with other plasma components. Sprague Dawley rats were dosed at 50 mg/kg lipid by an intravenous bolus via the lateral tail vein. Four to eleven rats were used for each liposome size prep. Blood samples were withdrawn at 0.5, 3.5, 6.5, and 24 hr post-injection by retro-orbital bleeding. The blood was spun in a table top centrifuge to remove the red blood cells. The amount of radiolabel in the plasma was determined by scintillation counting. The percent dose remaining in the plasma was calculated using a value of 3.08 ml plasma per 100 grams body weight.

The percent dose remaining in the plasma as a function of time was plotted for each liposome size. The area under the curve (AUC) for each liposome size was calculated by trapezoidal integration. The figure was produced by plotting the AUC for each liposome size versus the surface area weighted diameter for each liposome prep.

Figure 7:
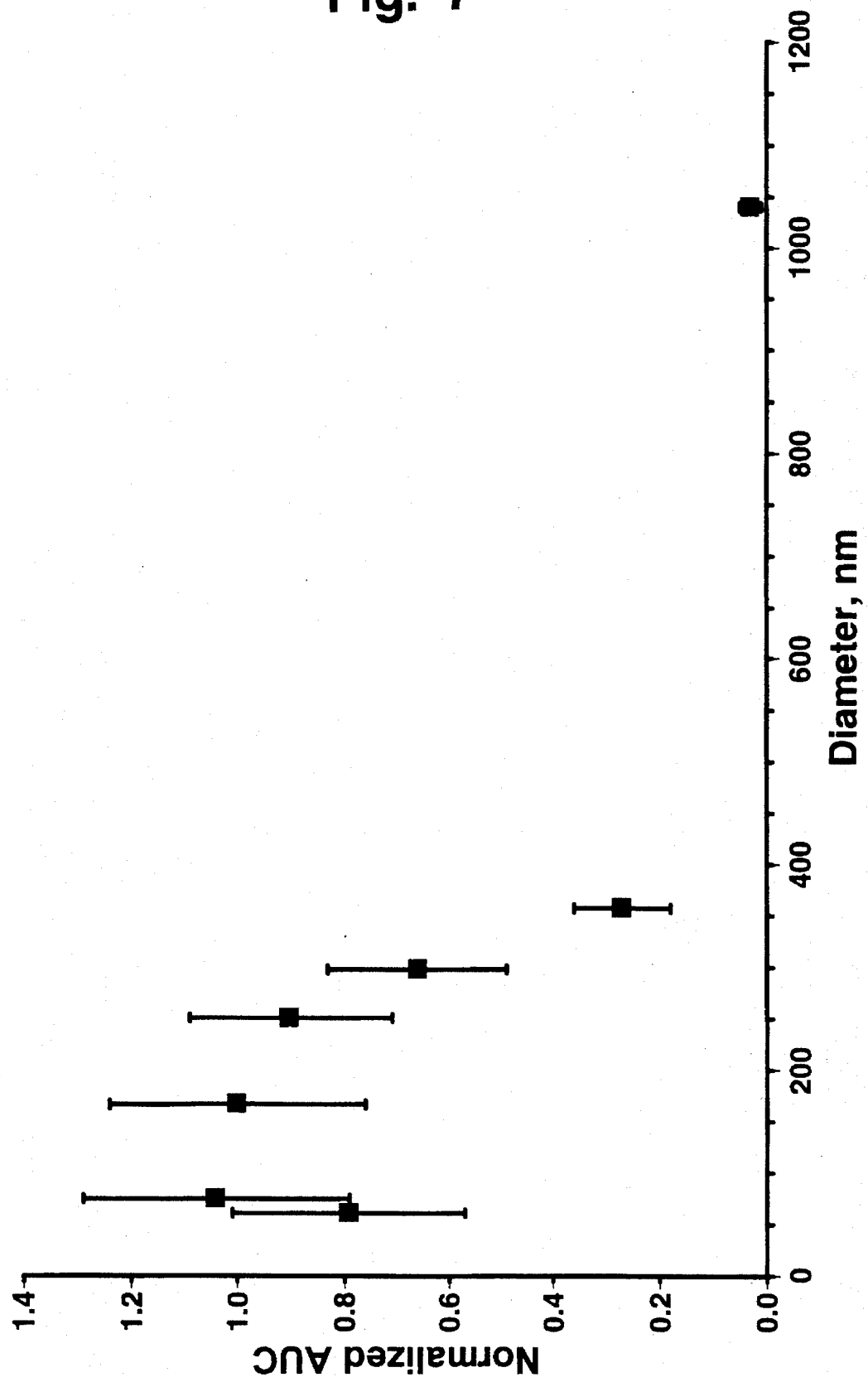
FIG. 7. Normalized AUC's (areas under the curves) as a Function of the Average Diameter of DSPC/N-Glutaryl-DPPE Liposomes. X-axis: liposome diameter (nm); y-axis: normalized AUC.
Figure 8:
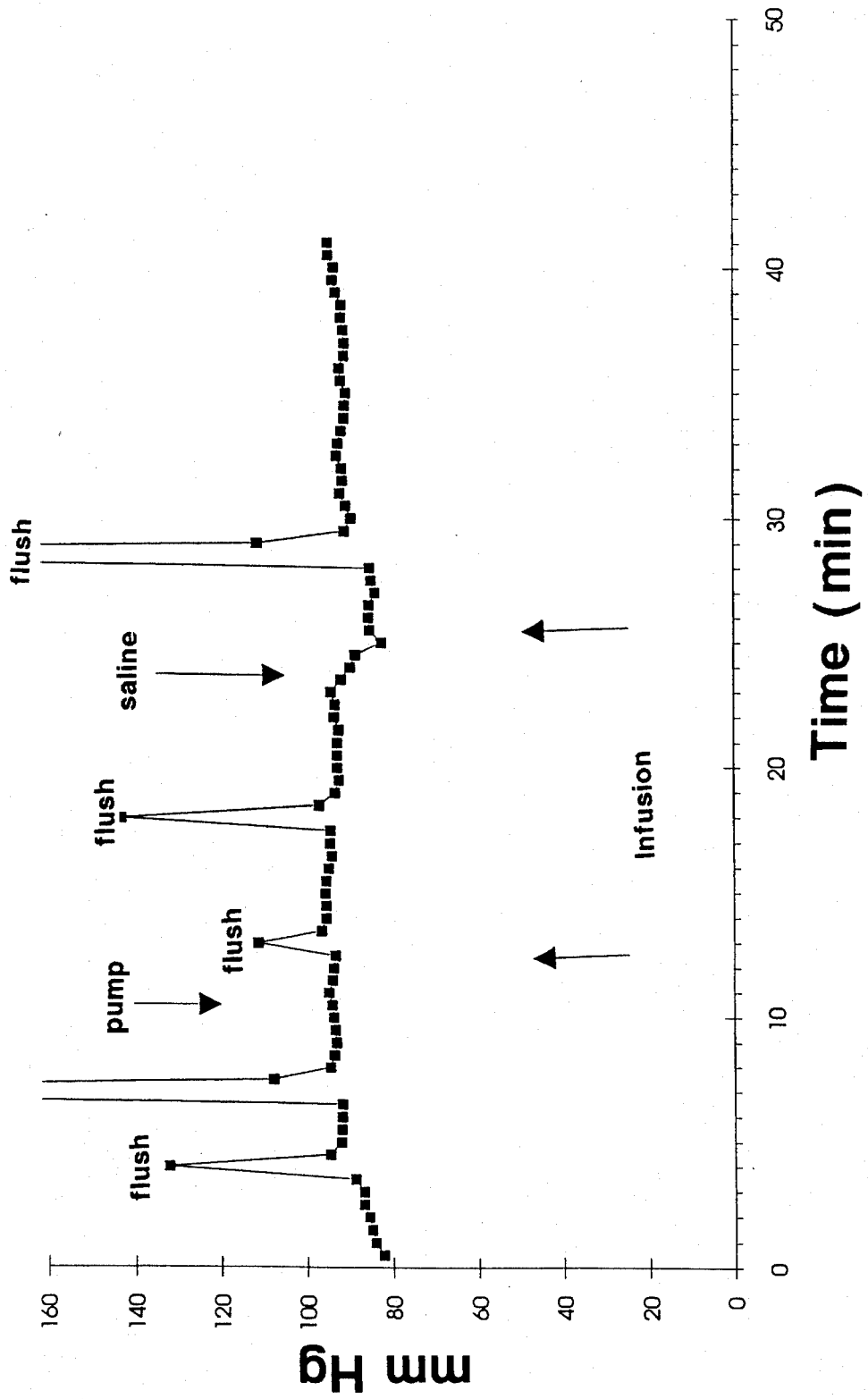
FIG. 8. Mean Blood Pressure During Infusion of DPPE-FGA Containing IF Liposomes into Rats. Data presented is for animal #1. X-axis: time (min) post-infusion; y-axis: blood pressure (mm Hg).
Figure 9:
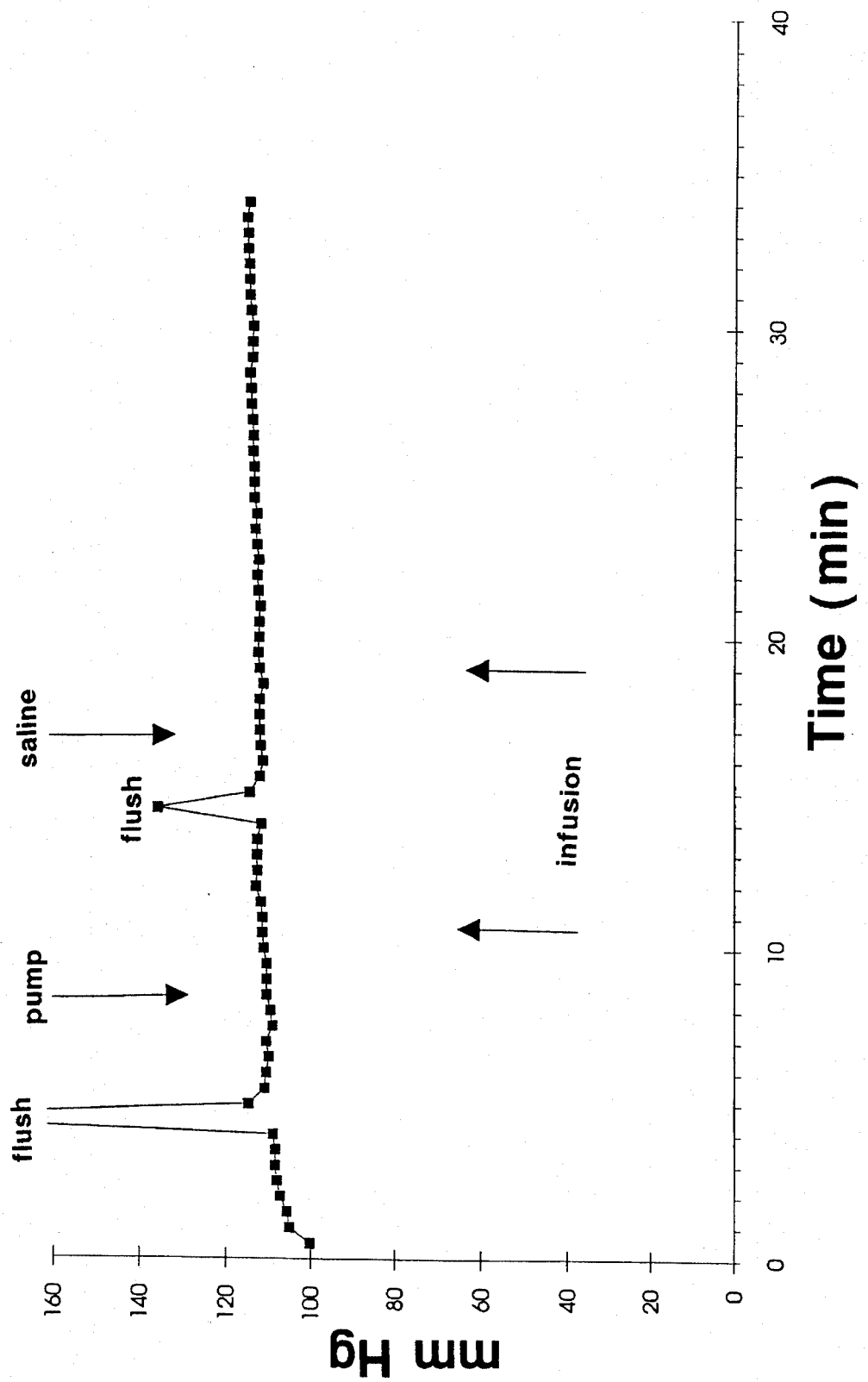
FIG. 9. Mean Blood Pressure During Infusion of DPPE-FGA IFs. Data presented is for animal #2.
Figure 10:
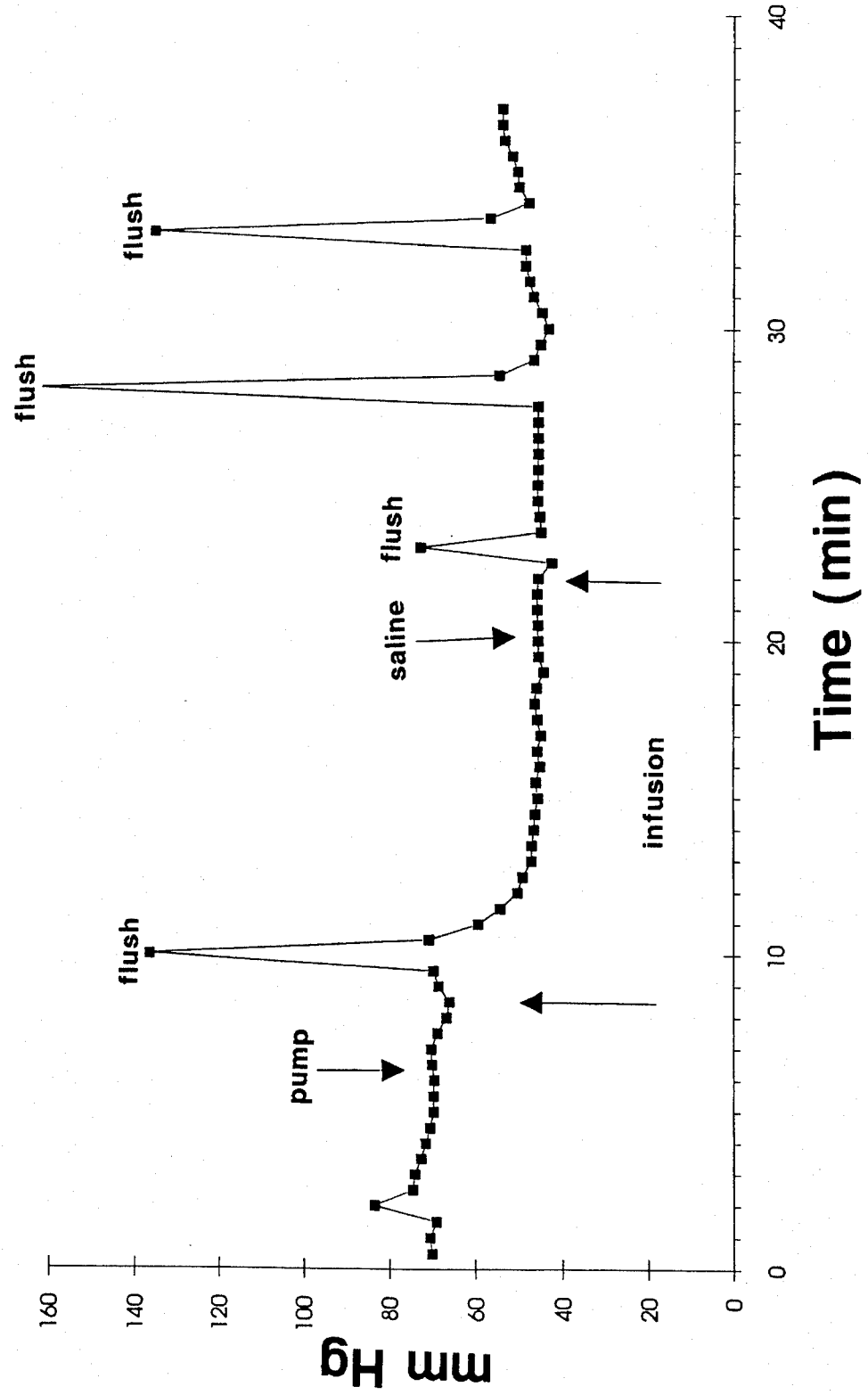
FIG. 10. Mean Blood Pressure During Infusion of DSPC (4.5) IF Liposomes. Data presented is for animal number 3.
Figure 11:
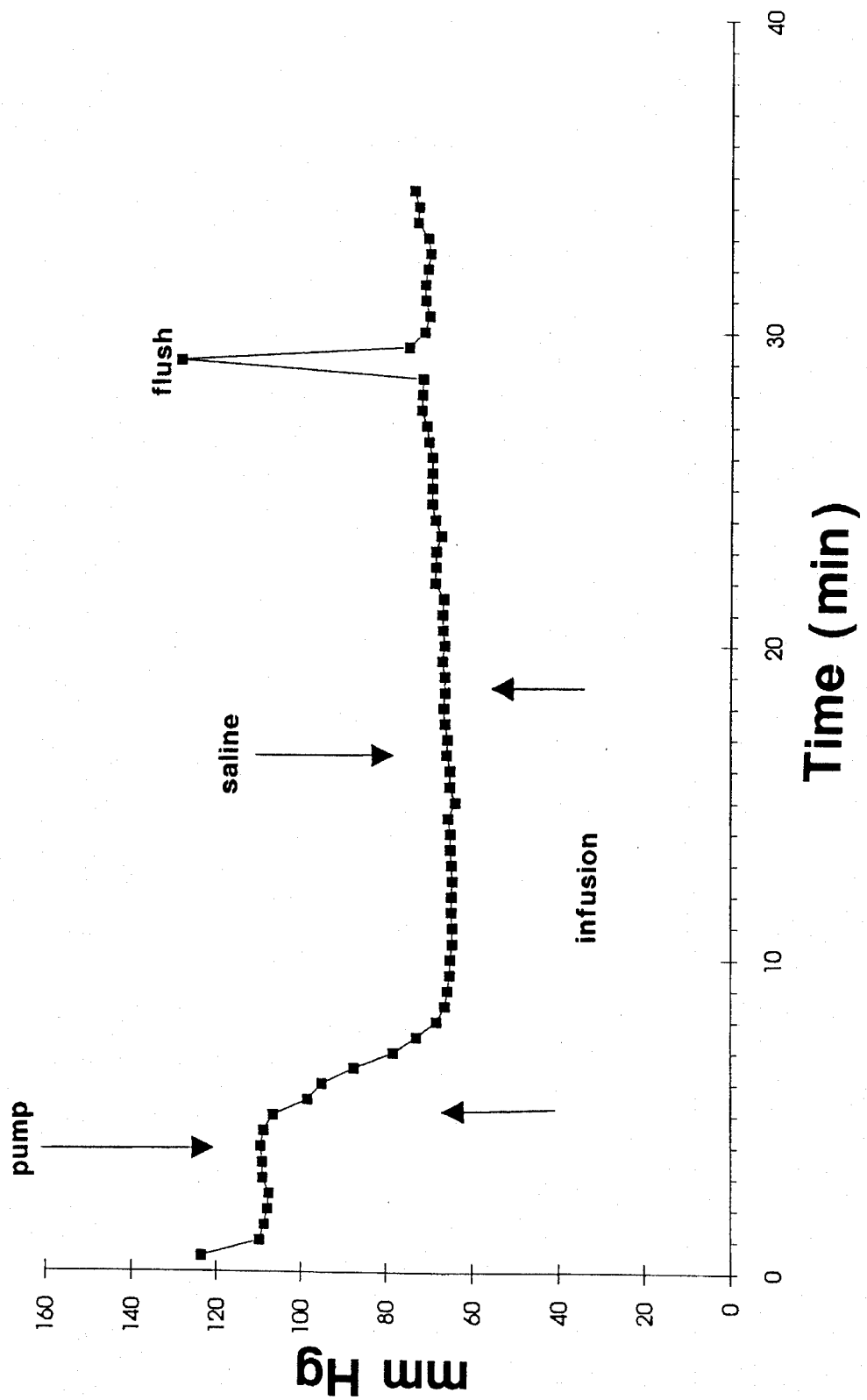
FIG. 11. Mean Blood Pressure During Infusion of DSPC (4.5) IF Liposomes. Data presented is for animal number 4.
Figure 12:
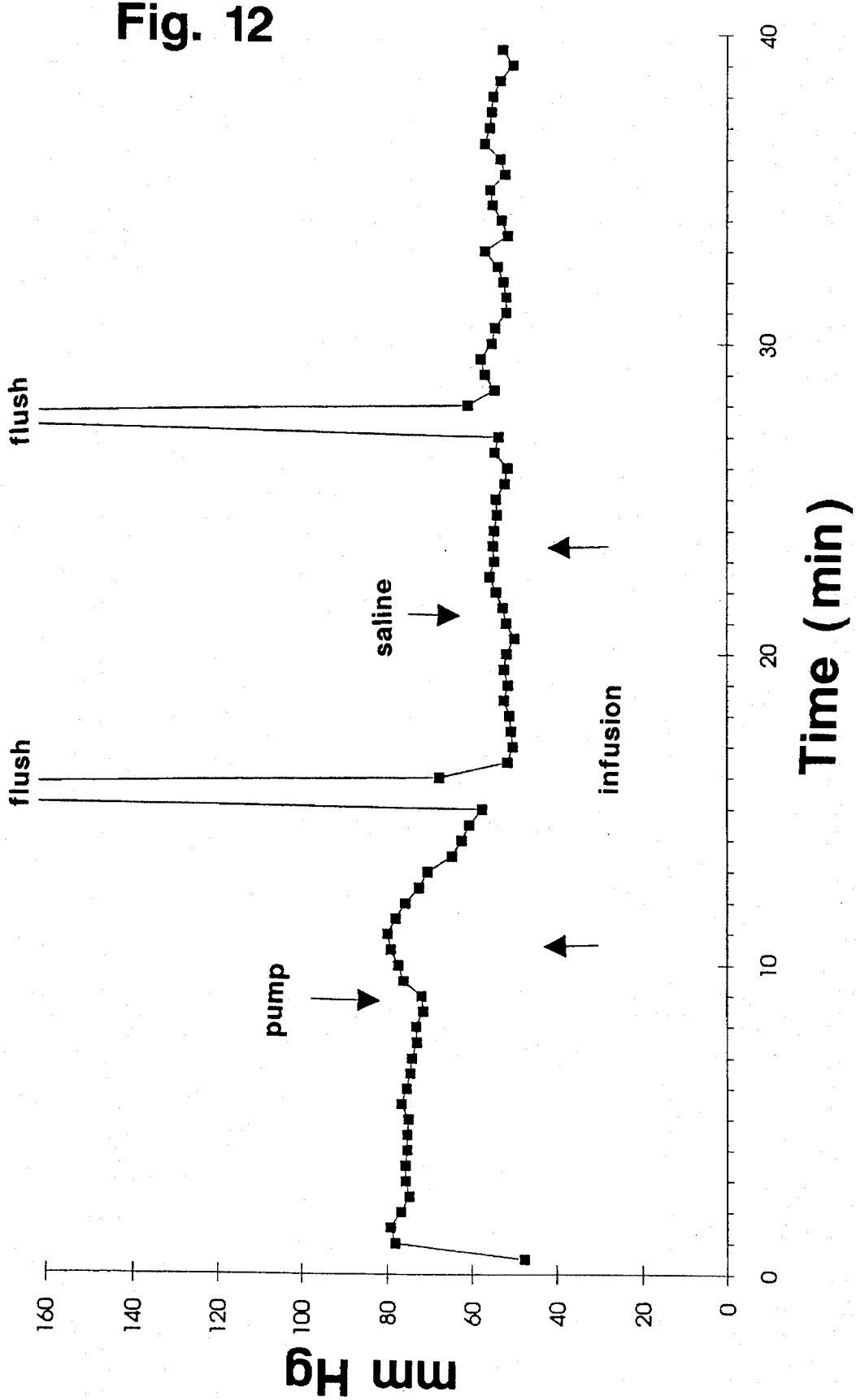
FIG. 12. Mean Blood Pressure During Infusion of DSPC (4.5) IF Liposomes. Data presented is for animal number 5.

FIG. 7 shows the normalized AUCs of DSPC IFVS and LUVETs, plotted as a function of surface area-weighted average diameter. The AUCs were calculated by trapezoidal integration of the circulation profiles of the IFVs and LUVETs, and were normalized to the AUC of the 200 nm pore size LUVET. The dots are normalized AUC's of DSPC IFVs and LUVETs (the surface area weighted diameter of disaggregated 200 nm pore size DSPC LUVETs was 197±93 nm, as determined by quasi-electric light scattering above the Tm of DSPC. However, actual particle size in plasma may be significantly larger due to DSPC LUVET aggregation).

Example 6

IF Liposomes Containing Fluorinated Glutaric Acid Derivatives

Synthesis

N-Fluoroglutaryl-DPPE

A suspension of DPPE (1 mmol) in dry ethyl acetate (100 ml) was heated to 80 deg. C. to dissolve the DPPE Triethylamine (4 mmol), and then hexafluoroglutaric anhydride (3 mmol), were added to this solution, followed by heating at 80–85 deg. C. for 6 hours. Gel filtration of the resulting crude material, using Sephadex LH-20 in chloroform:methanol (1:1), followed by silica gel column chromatography in chloroform:methanol:water (65:25:4), provided N-fluoroglutaryl-DPPE in 54% yield as a white crystalline material. This product was characterized by IR and NMR.

N-Fluorosuccinyl-DPPE

The same reaction conditions were utilized, except for the substitution of tetrafluorosuccinic anhydride for hexafluoroglutaric anhydride. The resulting compound was obtained in 44% yield, gave a single spot on thin layer chromatography and was characterized by IR and NMR.

N-Fluorobutyryl-DPPE

This compound was prepared by reacting DPPE with heptafluorobutyric anhydride, under the conditions described above. The resulting compound appeared as a single spot on TLC, was characterized by NMR and was obtained in 60% yield.

Blood Pressure Screening

Male Sprague-Dawley rats (Charles River) were anesthetized IP with sodium pentobarbital and abdominal aorta, plus external jugular, canulae were inserted surgically. The arterial canula was kept patent with two units of heparin, flushed once. Blood pressure was monitored by connecting a Winston Electronics model VT-15 blood pressure monitoring system to the arterial cannula. Baseline blood pressure was taken for several minutes before infusion of DPPE-FGA IF liposomes (interdigitation-fusion liposomes containing dipalmitoyl phosphatidylethanolamine/flouroglutaric acids); baseline blood pressure was determined as an average of four samples. The animals were given 50 mg/kg lipid at a rate of 4 mg/kg/min using a Harvard Pump 22 infusion pump, into the jugular vein. After infusion, the animals were monitored for about 15 minutes to observe the recovery phase. Blood pressure was monitored every 30 seconds on the VT-15 before, during and after IF infusion. Percent decrease from baseline blood pressure (baseline BP) was calculated as: [(baseline BP -peak depression BP)/baseline BP]×100. DPPE-FGA IF liposomes caused a 12% decrease in blood pressure from baseline in the first subject animal, and a 1.3% increase in the second subject (the average decrease was 5.3±9.24%). The date is presented in the following Table.

| Rat | Infusion | Blood Pressure (mm Hg) | | % Decrease |
|---|---|---|---|---|
| | | Pre-Infusion | Post-Infusion | |
| #1 | DPPE-FGA IFs | 93.40 | 82.40 | 11.80 |
| #2 | DPPE-FGA IFs | 110.00 | 111.40 | −1.27 |
| #3 | DSPC 4.5 | 70.00 | 42.30 | 39.60 |
| #4 | DSPC-4.5 | 108.20 | 63.80 | 41.00 |
| #5 | DSPC 4.5 | 73.60 | 49.90 | 32.20 |

Blood pressure during liposome infusion for each of these animals is presented in FIGS. 8–12 (for rats 1–5, respectively).

Example 7

Preparation and Use of Iotrolan, DPPE-GA Containing IF Liposomes

Small unilamellar liposomes (SUVs) containing DSPC (920 mg), with or without DPPE-GA (828 mg DSPC and 92 mg DPPE-GA), were prepared in $dH_2O$ or saline, respectively, at a lipid concentration of about 40 mg/ml and at a temperature of about 10 deg. C. above the lipid transition temperature (54 deg. C. for DSPC, the liposomes being prepared at 65–70 deg. C.). The lipid, or lipid mixture, was dissolved in methylene chloride and then dried to a thin film. DSPC liposomes were prepared by resuspending the dried lipid in 23 ml $dH_2O$, with heating to about 65 deg. C. for about 30 min (the heating step can be omitted if probe sonication is used to prepare the SUVs). DSPC/DPPE-GA liposomes were prepared by resuspending the dried lipids in saline at 65 deg. C.

An iotrolan suspension was prepared by mixing 46 mg iotrolan (300 mg/ml iodine), 16.3 ml ethanol and 6.7 ml $dH_2O$, adding the distilled water to the iotrolan before the ethanol and adding the ethanol slowly, with constant mixing.

Sixteen and one-half ml of the iotrolan suspension was aliquoted into each of four screw top tubes, and 5.5 ml of the SUV suspension was added. The resulting gels were mixed vigorously, and incubated at room temperature for at least one hour; DSPC/DPPE-GA liposomes were incubated at 30 deg. C. for 24 hours. After this, the tubes were incubated at 65–70 deg. C. for one hour. Each tube was then vortexed for 15 minutes.

Each sample was then mixed and sparged with a nitrogen stream, while being maintained at 65–70 deg. C., for about 111–13 minutes. The samples were then pooled in a 250-ml Erlenmeyer flask and allowed to cool to room temperature, to produce a clear solution with white foam on the surface. Sufficient quantity of the following buffer was added to the preparation to bring the volume to 200 ml: 2.4 mg/ml Tris base, 0.1 mg/ml Na/Ca EDTA, 0.9% NaCl (pH 7=7.4), and was mixed to produce an opaque, IF-containing suspension.

This suspension was centrifuged in 50-ml centrifuge bottles for at least about 5 minutes at about 3200 g. Centrifugation was repeated as need (for example, three cycles) to remove unentrapped iotrolan. The preparation was then assayed for lipid and iotrolan content, and characterized by electron microscopy, Malvern particle size distribution analysis, captured volume and lamellarity, and stored at room temperature until use.

Figure 13:
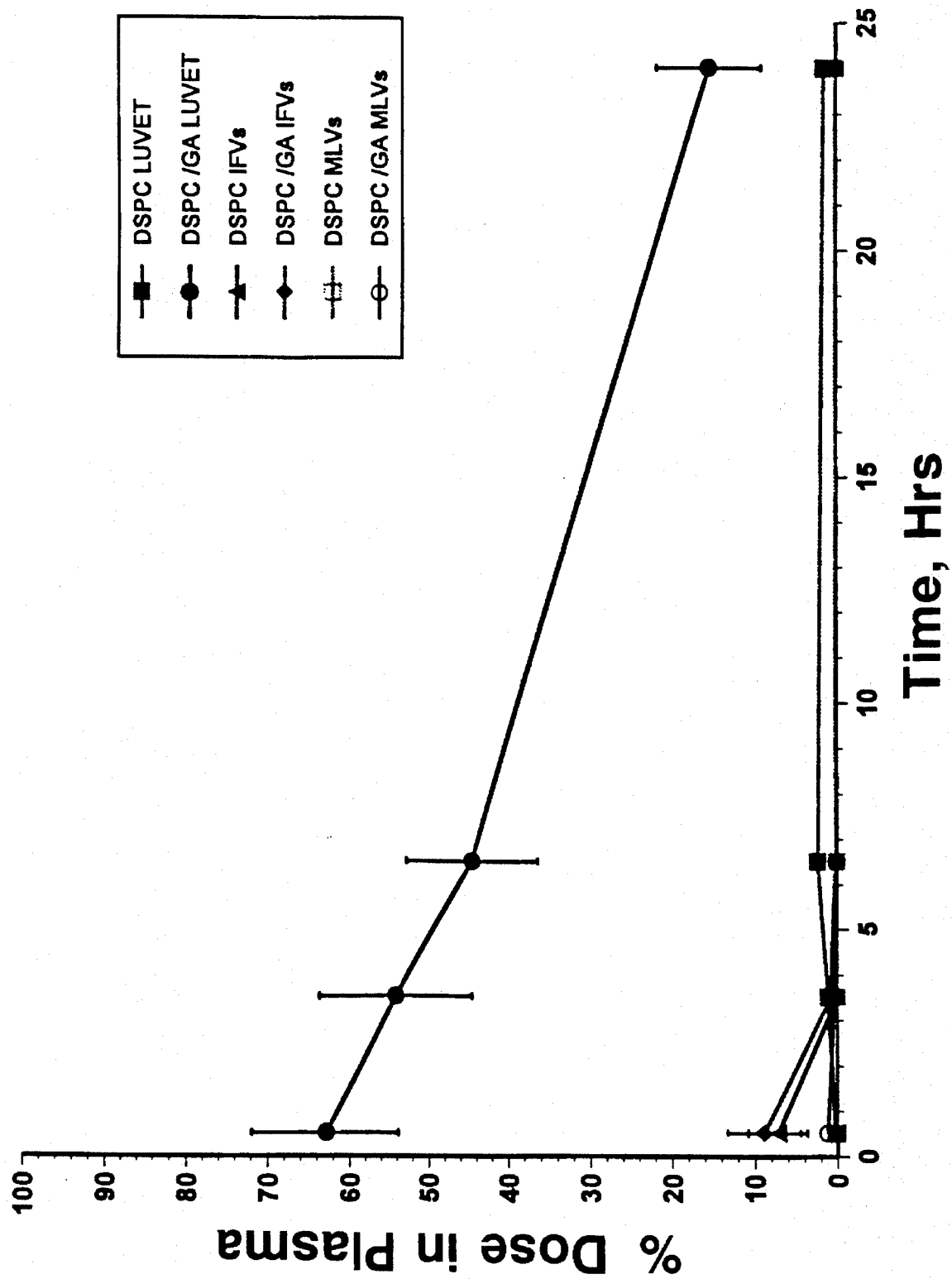
FIG. 13. Effect of DPPE-GA Incorporation Into Various Liposome Types. X-axis: time (hr.); y-axis: (% dose in plasma). Filled squares: DSPC LUVETs; filled circles: DSPC-DPPE/GA LUVETs; filled triangles: DSPC IFs; filled diamonds: DSPC-DPPE/GS IFs; open squares: DSPC multilamellar liposomes (MLVs); open circles: DSPC-DPPE/GA MLVs.

The percentage of injected liposomes (200 nm extruded vesicles) remaining in plasma, as a function of time, is given in FIG. 13 for various preparations, with and without DPPE-GA.

Figure 14:
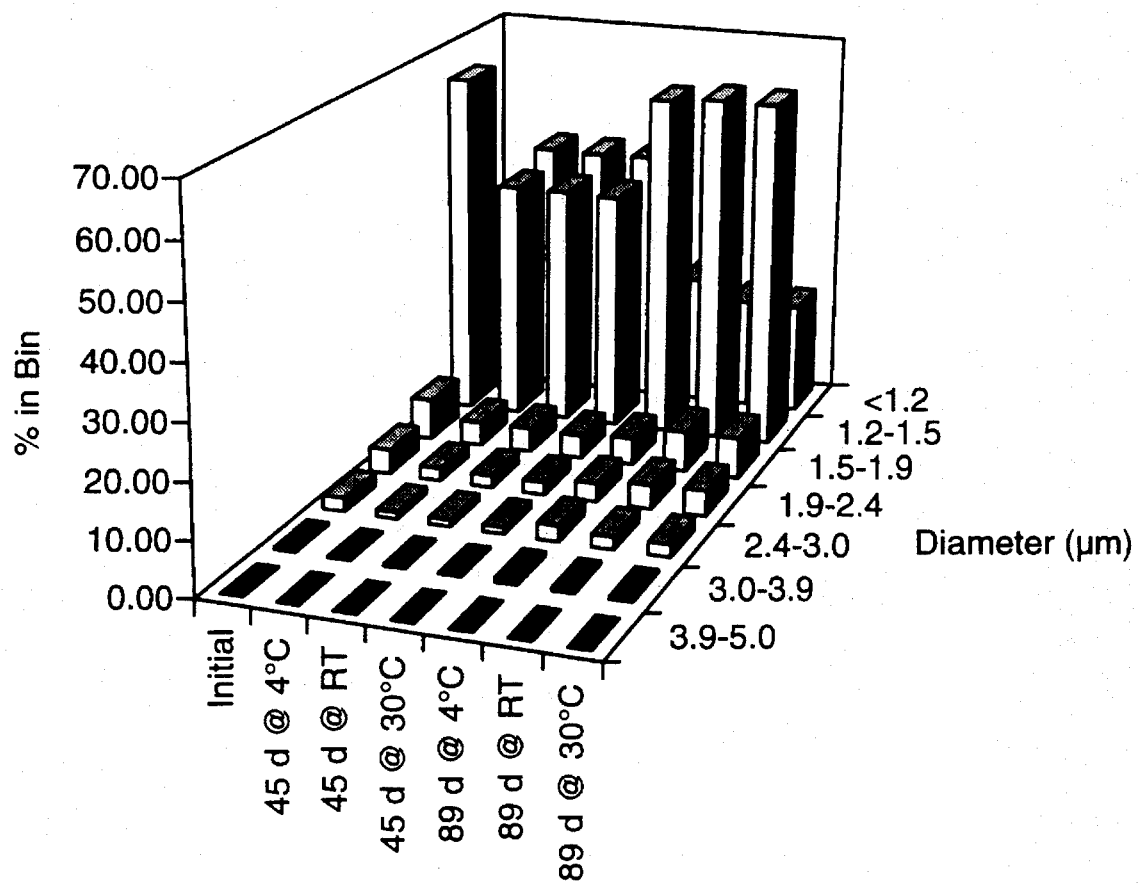
FIG. 14. Malvern Particle Size Distribution Analysis of DPPE-GA IFs Containing Iotrolan. X-axis: sample storage conditions; y-axis: % liposomes in Bin; z-axis: liposome diameter (microns). Data presented is for lot #1.
Figure 15:
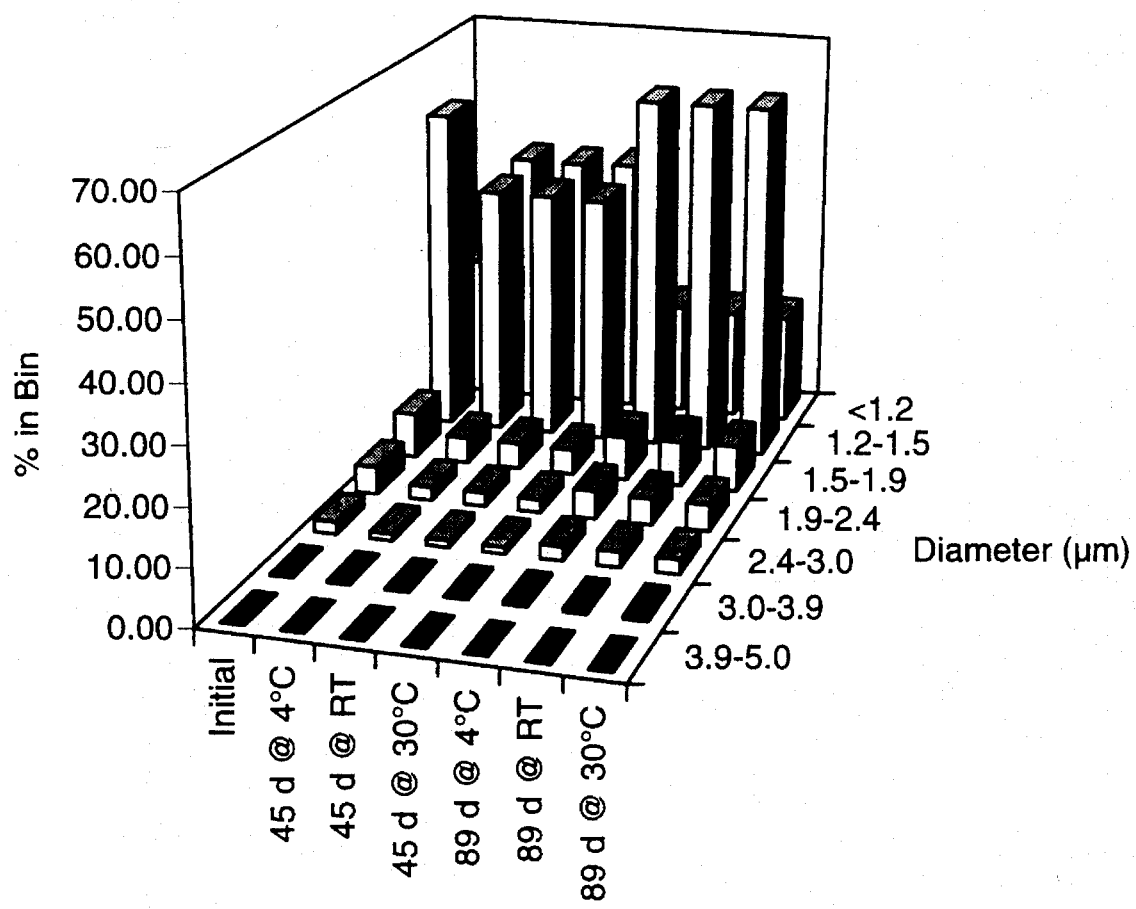
FIG. 15. Malvern Particle Size Distribution Analysis of DPPE-GA IFs Containing Iotrolan. X-axis: sample storage conditions; y-axis: % liposomes in Bin; z-axis: liposome diameter (microns). Data presented is for lot #2.

Table 4 (see below) gives CT scan results in rats using various lots of DSPC, DSPC/DPPE-GA (5 mole %) and DSPC/DPPE-GA (10 mole %) IF liposomes. FIGS. 14 and 15 present Malvern size distribution data for two of these lots. The following table presents a formulation summary for several of the lots.

| Lot# | Iodine mg/ml | Lipid (mg/ml) | Density (g/ml) | Captured Volume | Size | Lamellarity (% Lipid Out) |
|---|---|---|---|---|---|---|
| 1 | 100.5 | 16.3 | 1.09 | 18.6 | <5 μm | 53 |
| 2 | 100.5 | 16.8 | 1.09 | 20.9 | <5 μm | 45 |
| 3 | 104.6 | 16.5 | 1.10 | 20.6 | <5 μm | 50 |

The following tables present the pH, % iodine in supernatant, % lysophosphatidylcholine and CT results in rats dosed at 250 mg/kg iodine from stability samples, stored for various amounts of time, for various lots of DPPE-GA, iotrolan containing IFs. No change in color or appearance for any of the samples was observed.

| | | pH | | |
|---|---|---|---|---|
| | | Age (days) of sample/ Days at temperature | | |
| Lot# | Storage temp. | 0/0 | 92/45 | 125/78 |
| 1 | 4 deg. C. | NA | 7.1 | 7.1 |
| | room temp. | ND | 7.0 | 7.0 |
| | 30 deg. C. | NA | 7.0 | 7.1 |
| | | 0/0 | 56/45 | 89/78 |
| 2 | 4 deg. C. | NA | 7.1 | 7.2 |
| | room temp. | ND | 6.9 | 7.0 |
| | 30 deg. C. | NA | 7.1 | 7.0 |

| | | % Iodine in Supernatant | | |
|---|---|---|---|---|
| | | Age (days) of sample/ Days at temperature | | |
| Lot# | Storage temp. | 0/0 | 92/45 | 125/78 |
| 1 | 4 deg. C. | NA | 6.9 | 6.5 |
| | room temp. | ND | 6.8 | 7.1 |
| | 30 deg. C. | NA | 7.3 | 9.6 |
| | | 0/0 | 56/45 | 89/78 |
| 2 | 4 deg. C. | NA | 4.2 | 4.7 |
| | room temp. | ND | 4.2 | 4.6 |
| | 30 deg. C. | NA | 4.7 | 6.4 |

| | | % Lyso PC in Sample | | |
|---|---|---|---|---|
| | | Age (days) of sample/ Days at temperature | | |
| Lot# | Storage temp. | 0/0 | 92/45 | 125/78 |
| 1 | 4 deg. C. | NA | 3.4 | 7.1 |
| | room temp. | ND | 4.0 | 7.0 |
| | 30 deg. C. | NA | 3.6 | 7.1 |
| | | 0/0 | 56/45 | 89/78 |
| 2 | 4 deg. C. | NA | * | * |
| | room temp. | ND | * | 0.5 |
| | 30 deg. C. | NA | * | 1.7 |

-continued

| Lot # | Sample Age | Days at Temp. | Initial Value | 4 deg. C. | Room temp. | 30 deg. C. |
|---|---|---|---|---|---|---|
| 1 | 139 days | 92 days | 43.0 | 45.2 | 43.0 | 49.0 |
| 2 | 103 days | 92 days | 42.0 | 56.5 | ND | 56.5 |

CT Scan Results in Rats Using Stability Samples — Enhancement in Liver (ΔHU*)

Example 8

CT Imaging Study in Rabbits Using DPPE-GA, Iotrolan Containing IF Liposomes

DPPE-GA, iotrolan containing IF liposomes were prepared as described above, and contained 100.5 mg/ml iodine, 16.3 mg/ml lipid (iodine:lipid ratio of 6.2), had a density of 1.09 g/ml, captured volume of 18.6 (microliters per micromole lipid), and were less than 5 microns in diameter. Female rabbits weighing 4.5–5.8 kg were administered doses of such liposomes at 100 and 250 mg Iodine/kg body weight (one animal per dose) at a rate of 50 mg I/min×kg of body weight, and anesthetized with Xylazine/Ketamin.

Figure 16:
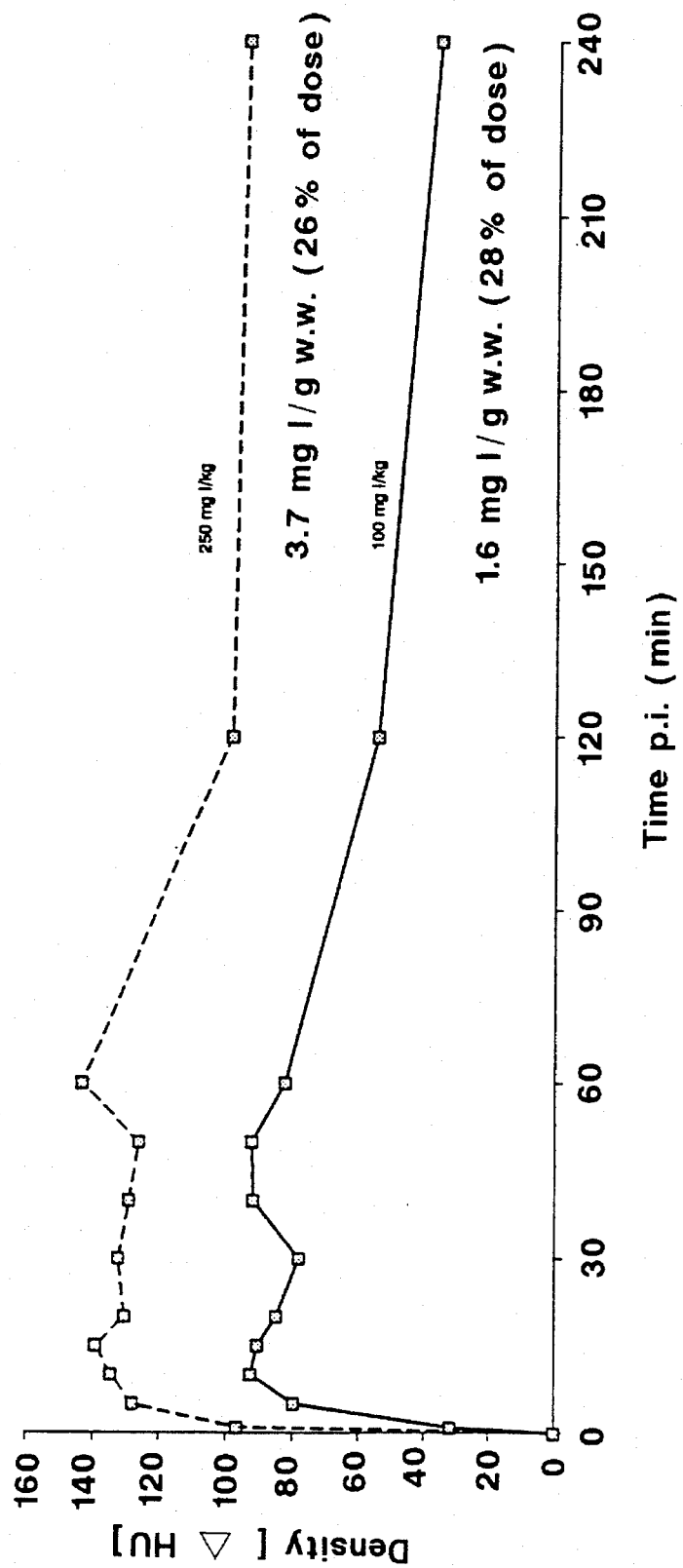
FIG. 16. CT Imaging Study of Rabbit Livers Using DPPE-GA, Iotrolan Containing IF Liposomes. X-axis: time post-injection (min.); y-axis: density ($\Delta$HU).

The densities of liver, spleen, aorta and kidney (cortex) were measured (in Hounsfield units—HU) before, and at various times after, intravenous liposome administration. Rabbits were sacrificed four hours after liposome administration. Iodine concentration was determined in liver, spleen, kidney, lung and blood. Results are presented in FIG. 16.

TABLE I

Iodine to Lipid Ratios for Iotrolan DSPC/DPPE-GA IFV's

| Formulation | Iodine/Lipid Ratio, w/w |
|---|---|
| DSPC IFV's | 4.5 |
| DSPC/DPPE-GA IFV's 5 mole % DPPE-GA | 5.9 |
| DSPC/DPPE-GA IFV's 10 mole % DPPE-GA | 5.7 |

TABLE 2

HU Enhancements in Rats Dosed with Iotrolan DSPC/DPPE-GA IFV's

| Formulation | Dose mg/Kg, Iodine | Time After Injection | Number of Rats | Liver HU Enhancement |
|---|---|---|---|---|
| DSPC IFV's | 100 | 1 Hr | 3 | 24 |
|  | 250 | 1 Hr | 3 | 48 |
| DSPC/DPPE-GA IFV's 5 mole % DPPE-GA | 100 | 1 Hr | 3 | 35 |
|  | 250 | 1 Hr | 3 | 58 |
|  | 250 | 3 Hr | 3 | 71.3 |
| DSPC/DPPE-GA IFV's 10 mole % DPPE-GA | 100 | 1 Hr | 3 | 31 |
|  | 250 | 1 Hr | 3 | 51 |
|  | 100 | 1 Hr | 3 | 31 |
|  | 250 | 1 Hr | 3 | 52 |
|  | 250 | 3 Hr | 4 | 56 |

TABLE 3

Mean Arterial Blood Pressure Response of Rats Dosed with DSPC/DPPE-GA IFV's

| Formulation | Rat # | Baseline Pre-injection mm Hg | Baseline Post-injection mm Hg | Absolute Diference, mm Hg | % Decrease from Pre-injection Baseline | Average % Decrease for Formulation |
|---|---|---|---|---|---|---|
| DSPC IFV's (Control) | 2 | 162 | 80 | 82 | 51 |  |
|  | 10B | 176 | 78 | 98 | 56 |  |
|  | 9B | 172 | 67 | 105 | 61 |  |
|  |  |  |  |  |  | 56.0 +/− 5.0 |
| DSPC/DPPE-GA IFV's 10 mole % DPPE-GA | 6 | 143 | 129 | 14 | 10 |  |
|  | 8 | 134 | 126 | 8 | 6 |  |
|  | 8B | 157 | 143 | 14 | 9 |  |
|  |  |  |  |  |  | 8.3 +/− 2.1 |
| DSPC/DPPE-GA IFV's 5 mole % DPPE-GA | 11 | 122 | 104 | 18 | 15 |  |
|  | 4 | 120 | 98 | 22 | 18 |  |
|  | 14 | 118 | 94 | 24 | 20 |  |
|  | 6B | 165 | 124 | 41 | 25 |  |
|  |  |  |  |  |  | 19.5 +/− 4.2 |
| DSPC/DPPE-GA IFV's 2 mole % DPPE-GA | 12 | 134 | 100 | 34 | 25 |  |
|  | 13 | 96 | 74 | 22 | 23 |  |
|  | 4B | 157 | 104 | 53 | 34 |  |
|  |  |  |  |  |  | 27.3 +/− 5.9 |
| Saline | 11B | 151 | 147 | 4 | 3 |  |
|  | 1S | 122 | 122 | 0 | 0 |  |
|  |  |  |  |  |  | 1.5 |

| | Iotrolan Liposome Product Candidate Summary of CT Results in Rats | | | | | |
|---|---|---|---|---|---|---|
| Lipid | | | HU above Baseline in Liver | | | |
| Components | t in hours | n | 250 mg/Kg I | 100 mg/Kg I | Lot # | I:L |
| DSPC | 1 | 3 | 91 | 44 | FMF04293 | 4.7 |
| DSPC/ | 1 | 3 | 52 | 31 | SM10A1693 | 5.7 |
| DPPE-GA | 1 | 3 | 43 | 26 | FMJ0693 | 6.2 |
| (10 mole %) | 1 | 3 | 42 | 27 | FMK1193 | 6.0 |
| | 1 | 3 | 50 | 31 | FML1093 | 6.3 |
| | 3 | 4 | 56 | not done | SM10A1693 | 5.7 |
| DSPC/ | 1 | 3 | 58 | 35 | SM5A1693 | 5.9 |
| DPPE-GA | 3 | 3 | 72 | not done | SM5A1693 | 5.9 |
| (5 mole %) | | | | | | |

What is claimed is:

1. A method reducing a blood pressure decrease associated with administration of a liposome to an animal which comprises incorporating a surface agent-modifying lipid which is a phosphatidylethanolamine conjugated to a dicarboxylic acid into a liposome such that the surface agent-modifying lipid comprises at least about 10 mole percent of the liposome's bilayer and administering the liposome to the animal, wherein the liposome has an average diameter of from about 200 nm to about 5000 nm.

2. The method of claim 1, wherein the liposome (has a diameter of from about 200 nm to about 5000 nm) comprises a bioactive agent.

3. The method of claim 1, wherein the liposome has a diameter of from about 400 nm to about 5000 nm.

4. The method of claim 3, wherein the liposome has a diameter of from about 400 nm to about 1000 nm.

5. The method of claim 1, wherein the liposome is a large unilamellar liposome.

6. The method of claim 1, wherein the liposome is a multilamellar liposome.

7. The liposome of claim 6, wherein the multilamellar liposome comprises a solute entrapped in its aqueous compartments and wherein the concentration of the solute in each of the aqueous compartments is substantially equal.

8. The method of claim 1, wherein the dicarboxylic acid is succinic acid, glutaric acid, adipic acid, bimelic acid, suberic acid, tartaric acid, mucic acid, tetrafluorosuccinic acid or hexafluoroglutaric acid.

9. The method of claim 8, wherein the dicarboxylic acid is glutaric acid.

10. The method of claim 1, wherein the phosphatidylethanolamine has saturated acyl chains.

11. The method of claim 10, wherein the phosphatidylethanolamine is dipalmitoyl phosphatidylethanolamine (DPPE).

12. The method of claim 1, wherein the surface agent-modifying lipid further comprises a spacer group and wherein the spacer group comprises one or more organic functional groups capable of attaching to the glycerol backbone and the amino group of the phosphatidylethanolamine.

13. The method of claim 12, wherein the functional group is an hydroxyl, thiol, epoxide or amine group.

14. The method of claim 12, wherein the spacer group is ethylene glycol or polyethylene glycol.

15. The method of claim 2, wherein the bioactive agent is a contrast agent, antibacterial agent, antiviral agent, antifungal agent, anti-parasitic agent, tumoricidal agent, immunomodulator, vasodilator, radiolabel, radio-opaque compound, fluorescent compound, or anti-inflammatory agent.

16. The method of claim 15, wherein the bioactive agent is a water-soluble iodinated contrast agent selected from the group consisting of iohexol, iopamidol, ioxoglate, iotrolan, ioversol, iothalamate, iodimide, iodipamide, iopromide, metrizamide, iopentol, iodixanol, diatrizoate, iotroxic acid and mixtures and pharmaceutically acceptable salts thereof.

17. The method of claim 16, wherein the water-soluble iodinated contrast agent is iotralan.

18. The method of claim 1, wherein the liposome composition is administered by intravenous or intra-arterial administration.

* * * * *